(12) United States Patent
Pereira et al.

(10) Patent No.: US 7,947,811 B2
(45) Date of Patent: May 24, 2011

(54) ANTIBODIES THAT BIND SPECIFICALLY TO HUMAN RON PROTEIN

(75) Inventors: Daniel Pereira, Mississauga (CA); Jennifer O'Toole, Rockaway Park, NY (US)

(73) Assignee: ImClone LLC, New York, NY (US)

( * ) Notice: Subject to any disclaimer, the term of this patent is extended or adjusted under 35 U.S.C. 154(b) by 158 days.

(21) Appl. No.: 12/313,589

(22) Filed: Nov. 21, 2008

(65) Prior Publication Data

US 2009/0136510 A1 May 28, 2009

Related U.S. Application Data

(60) Provisional application No. 60/989,558, filed on Nov. 21, 2007.

(51) Int. Cl.
*C07K 16/28* (2006.01)
*C07K 16/00* (2006.01)
*A61K 39/395* (2006.01)

(52) U.S. Cl. ............. 530/388.22; 530/387.1; 530/388.1; 530/388.15; 424/130.1; 424/141.1; 424/143.1

(58) Field of Classification Search .................. None
See application file for complete search history.

(56) References Cited

U.S. PATENT DOCUMENTS

| | | | |
|---|---|---|---|
| 3,773,919 | A | 11/1973 | Boswell et al. |
| 4,275,149 | A | 6/1981 | Litman et al. |
| 4,946,778 | A | 8/1990 | Ladner et al. |
| 5,616,582 | A | 4/1997 | Barker |
| 5,861,301 | A | 1/1999 | Terman et al. |
| 6,165,464 | A | 12/2000 | Hudziak et al. |
| 2003/0073656 | A1 | 4/2003 | Waltz et al. |
| 2004/0101920 | A1 | 5/2004 | Radziejewski et al. |
| 2004/0185506 | A1 | 9/2004 | Heavner |
| 2004/0259156 | A1 | 12/2004 | Zhu |

FOREIGN PATENT DOCUMENTS

| | | |
|---|---|---|
| WO | 8809344 | 12/1988 |
| WO | 9201047 | 1/1992 |
| WO | 92/14748 | 9/1992 |
| WO | 9311236 | 6/1993 |
| WO | 9630347 | 10/1996 |
| WO | 9633980 | 10/1996 |
| WO | 0211677 | 2/2002 |
| WO | 02083047 | 10/2002 |
| WO | WO02083074 | 10/2002 |
| WO | 02102973 | 12/2002 |
| WO | 03075840 | 9/2003 |
| WO | 2005016970 | 2/2005 |
| WO | 2005120557 | 12/2005 |
| WO | WO2005120557 | 12/2005 |

OTHER PUBLICATIONS

The Merck Manuals Online Medical Library, [online]. Whitehouse Station, NJ: Merck Research Laboratories, 2006-2007. [retrieved on Oct. 7, 2010]. Retrieved from the Internet: < URL: http://www.merck.com/mmpe/print/sec02/ch021/ch021h.html>. Colorectal Cancer. see pp. 1-7.*
Skeel, J. Immunol. 152:4618-4623 (1994).
Smith and Johnson, Gene 67(1):31-40 (1998).
Southern and Berg, J. Mol Appl. Genet. 1:327-341 (1982).
Subramani et al, Mol. Cell. Biol. 1:854-864 (1981).
Suzuki Biomed Res. Apr; 29 (2):77-84 (2008.
Terman et al., Oncogene 6:1677-1683 (1991).
Thomas et al., Cancer Res., 67(13):6075-6082 (2007).
Urlaub and Chasin, Proc. Natl. Acad. Sci. USA 77: 4216-20 (1980).
Wang et al, Blood, 104(9):2893-2902 (2004).
Wang et al. Scand. J. Immunol., Blackwell Sci. Pub. Oxford, GB 56(6):545-553 (2002).
Wang et al., Experimental Cell Research 226:39-46 (1996).
Wang, et al., Oncogene 13:2167-2175 (1996).
Wang, J. Biol. Chem. 269:14027-14031(1994).
Welm et al., PNAS 104(18):7570-7575 (2007).
Willet et al., Am. J. Respir.Cell Mol. Biol. 18:489-496 (1998).
Wu et al., Clin. Cancer Res. 12(21):6573-6584 (2006).
Xu et al., Oncogene 23(52):8464-8474 (2004).
Yang et al., J. Mol. Biol., 254:392-403 (1995).
Zhou et al., Oncogene 22:186-197 (2003).
Zinser et al, Cancer Res., 66(24):11967-11974 (2006).
Abath & Simpson Pept. Res. 3(9): 167-8 (1990).
Anido et al, Abstract 1712 presented at the 37th Annual Meeting of ASCO, San Francisco, CA, May 12-15, 2001.
Arnon et.al., Adv. Exp. Med. Biol. 303:79-90 (1991).
Bately et al., Life Sci. 62:143-50 (1998).
Camp et al., American Cancer Society 109(6):1030-1039 (2007).
Chen et al., Carcinogenesis 23(11):1811-1819 (2002).
Chen et al., Experimental Cell Research 261:229-238 (2000).
Chen et al., Oncogene, 21: 6382-6386 (2002).
Christiansen et al., Cancer Res. 63(21):7345-55 (2003).
Davies et al., Immunotech. 2(3):169-179 (1996).
Dieckmann and Tzagoloff J. Biol. Chem. 260:1513-1520 (1985).
Ganesan, Drug Discov. Today 7(1): 47-55 (2002).
Gaudino, Oncogene 11(12):2627-37 (1995).
Greenfield et.al., Cancer Research 50:6600-07 (1990).
Harlow & Lane ed. Antibodies: A Laboratory Manual, Cold Spring Harbor, 211-213 (1998).
Hawkins et al., J. Mol. Bio. 226:889-896 (1992).
Hermentin and Seiler, Behring Inst. Mitt. 82:197-215(1988).
Hidalgo et al., Abstract 281 presented at the 37th Annual Meeting of ASCO, San Francisco, CA, (May 12-15, 2001).
Hochleitner et al., Protein Science 9(3):487-496 (2000).
Holt, Trends in Biotechnology 21(11): 484-490 (2003).
Iwama et al., Blood 86:3394-3403 (1995).
Kaufmann and Sharp J. Mol. Biol. 159:601-664 (1982).
Kiseleva et al., Mol. Biol. (USSR) 25:508-14 (1991).
Leonard, Adv. Cancer Res. 77:139-167 (2000).

(Continued)

*Primary Examiner* — Sharon Wen
(74) *Attorney, Agent, or Firm* — Nicole S. Woods

(57) ABSTRACT

The invention provides antibodies or fragments thereof, including human antibodies, specific for Macrophage-Stimulating Protein Receptor (MSP-R or RON), which inhibit RON activation. Also provided are methods to inhibit RON, particularly the use of RON antibodies to treat diseases such as cancer.

7 Claims, 22 Drawing Sheets

OTHER PUBLICATIONS

Leonis et al, Future Oncol. 3(4):441-448 (2007).
Little et al., Immunol. Today 21(8):364-370 (2000).
Lou, Drug Discov. Today 6(24):1288-1294 (2001).
Low et al., J. Mol. Bio. 250:359-368 (1996).
Maggiora et al., Experimental Cell Research 288:382-389 (2003).
Maggiora et al., Oncogene 16:2927-2933 (1998).
Montero, et al. Hybridoma 17(6):541-551 (1998).
Moyer et al., Cancer Res., 57:4838-48 (1997).
O'Toole et al.; Cancer Res., 66(18):9162-9170 (2006).
Okino et al., Digestive Diseases & Sciences 46(2):424-429 (2001).
Okino et al., Int. J. Oncol. 15:709-714 (1999).
Panek et al., J Pharmacol. Exp. Thera 283:1433-44 (1997).
Patton, J Surg Pathol., 28(8):1045-50 (2004).
Peace et al., Oncogene 20(43):6142-6151(2001).
Pearson & Lipman, PNAS USA 85:2444-8 (1988).
Pedley et al, Br. J. Cancer 68:69-73(1993).
Periera et al., Euro. J. Cancer Supp. 2(8):94 (2004).
Pollack et al., J. Pharmacol. Exp. Ther. 291(2):739-748 (1999).
Reineke, Methods of Molecular Biology 248:443-63 (2004).
Rowinsky et al., Abstract 5, 37th Annual Meeting of ASCO, San Francisco, CA, (May 12-15, 2001).
Sambrook et al., Molecular Cloning: A Laboratory Manual, 2nd Edition, Cold Spring Harbor Laboratory Press (1989).
Santoro et al., Molecular and Cellular Biology 16(12):7072-7083 (1996).
Scahill et al., Proc. Natl. Acad. Sci. USA 80:4654-59 (1983).
Secco et al., J. Immunol. Methods 285(1):99-109 (2004).
Shibuya et al., Oncogene 5: 519-24 (1990).
Skeel, Exp. Cell Res. 102:434-438 (2000).
Ausubel, et al., Current Protocols in Molecular Biology, vol. I, 2.10.3 (1989).
Camp, et al., Annals of Surgical Oncology 12(4):273-281 (2005).
Chen, et al., Carcinogenesis 23(11):1811-1819 (2002).
Davies, et al., Immunotech. 2(3):169-179 (1996).
Holt, et al., Trends in Biotech. 21(11):484-490 (2003).
Lee, et al., Oncogene 8(12):3403-3410 (1993).
Little, et al., Immun. Today 21(8):364-370 (2000).
Montero-Julian, et al., Hybridoma 17(6):541-551 (1998).
O'Toole, et al., 2008, AACR, San Diego, CA, In Vitro Characterization and In Vivo Anti-tumor Activity of Human Monoclonal Antibodies to the RON Receptor Tyrosine Kinase.
O'Toole, et al., Cancer Res 66(18):9162-9170 (2006).
Peace, et al., Oncogene 20(43):6142-6151 (2001).
Pereira, et al., European J. of Cancer, Suppl 2(8):94 (2004).
Ronsin, et al., Oncogene 8(5):1195-1202 (2004).
Wang, et al., Carcinogenesis 21:1507-1512 (2000).
Wang, et al., Scan. J. Immunol. 56(6):545-553 (2002).
Xu, et al., Oncogene 23(52):8464-8474 (2004).

\* cited by examiner

FIG. 1A

```
    Q   V   Q   L   V   Q   S   G   P   E   V   K   K   S   G   S   S   V   K   V
 1  CAG GTC CAG CTG GTG CAG TCT GGA CCT GAG GTG AAG AAG TCT GGG TCC TCG GTG AAG GTC

S   C   K   A   S   G   G   T   F   S   S   D   A   I   T   W   V   R   Q   A
61  TCC TGC AAG GCT TCT GGA GGC ACC TTC AGC AGC GAT GCT ATC ACC TGG GTG CGA CAG GCC

P   G   Q   G   L   E   W   M   G   G   I   I   P   I   L   G   M   A   N   Y
121 CCT GGA CAA GGG CTT GAG TGG ATG GGA GGG ATC ATC CCT ATC CTT GGT ATG GCA AAC TAC

A   Q   K   F   Q   G   R   V   T   I   T   A   D   K   S   T   N   T   A   Y
181 GCA CAG AAG TTC CAG GGC AGA GTC ACG ATT ACC GCG GAC AAA TCC ACG AAC ACA GCC TAC

M   E   L   S   S   L   R   S   E   D   T   A   V   Y   F   C   A   R   V   A
241 ATG GAG CTG AGC AGC CTG AGA TCT GAG GAC ACG GCC GTG TAT TTT TGT GCG AGA GTG GCC

D   Y   Y   G   S   L   G   T   Y   Y   W   Y   F   D   L   W   G   R   G   T   L
301 GAT TAC TAT GGT TCG TTG GGG ACT TAC TGG TAC TTC GAT CTC TGG GGC CGT GGC ACC CTG

V   T   V   S   S  (SEQ ID NO:2)
361 GTC ACT GTC TCC TCA (SEQ ID NO:1)
```

FIG. 1B

```
      E   I   V   L   T   Q   S   P   G   T   L   S   L   S   P   G   E   R   A   T
  1  GAA ATT GTG TTG ACG CAG TCT CCA GGC ACC CTG TCT TTG TCT CCA GGG GAA AGA GCC ACC

L   S   C   R   A   S   Q   S   V   S   S   Y   L   A   W   Y   Q   Q   K
 61  CTC TCC TGC AGG GCC AGT CAG AGT GTT AGC AGC TAC TTA GCC TGG TAC CAG AAA

P   G   Q   A   P   R   L   L   I   Y   G   A   S   S   W   A   T   G   I   P
121  CCT GGC CAG GCT CCC AGG CTC CTC ATC TAT GGT GCA TCC AGC TGG GCC ACT GGC ATC CCA

D   R   F   S   G   S   G   S   G   T   D   F   T   L   T   I   S   R   L   E
181  GAC AGG TTC AGT GGC AGT GGG TCT GGG ACA GAC TTC ACT CTC ACC ATC AGC AGA CTG GAG

P   E   D   F   A   V   Y   Y   C   Q   Q   Y   G   S   S   P   L   T   F   G
241  CCT GAA GAT TTT GCA GTG TAT TAC TGT CAG CAA TAT GGT AGC TCA CCT CTC ACT TTC GGC

G   G   T   K   V   E   I   K   (SEQ ID NO:4)
301  GGA GGG ACC AAG GTG GAG ATC AAA (SEQ ID NO:3)
```

FIG. 1C

```
     E   V   Q   L   V   E   S   G   G   G   L   V   Q   P   G   G   S   L   R   L
  1  GAG GTG CAG CTG GTG GAG TCT GGG GGA GGC TTG GTC CAA CCT GGG GGG TCC CTG AGA CTC

S   C   A   A   S   G   F   T   F   S   S   Y   L   M   T   W   V   R   Q   A
 61  TCC TGT GCA GCC TCT GGA TTC ACC TTT AGT AGT TAT TTA ATG ACC TGG GTC CGC CAG GCT

P   G   K   G   L   E   W   V   A   V   N   I   K   Q   D   G   S   E   K   Y   Y
121  CCA GGG AAA GGG CTG GAG TGG GTG GCC GTG AAT ATA AAG CAA GAT GGA AGT GAG AAA TAC TAT

V   D   S   V   K   G   R   F   T   I   S   R   D   N   A   K   N   S   L   Y
181  GTG GAC TCT GTG AAG GGC CGA TTC ACC ATC TCC AGA GAC AAC GCC AAG AAC TCA CTG TAT

L   Q   M   N   S   L   R   A   E   D   T   A   V   Y   Y   C   T   R   D   G
241  CTG CAA ATG AAC AGT CTG AGA GCC GAG GAC ACG GCT GTG TAT TAT TGT ACG AGG GAT GGC

Y   S   G   R   H   Y   G   M   D   V   W   G   Q   G   T   T   V   T   V
301  TAT AGT GGG AGA CAC TAC GGT ATG GAC GTC TGG GGC CAA GGG ACC ACG GTC ATC GTC

S   S   (SEQ ID NO:6)
361  TCC TCA (SEQ ID NO:5)
```

FIG. 1D

```
      E   I   V   L   T   Q   S   P   A   T   L   S   L   S   P   G   E   R   A   T
  1  GAA ATT GTG TTG ACA CAG TCT CCA GCC ACC CTG TCT TTG TCT CCA GGG GAA AGA GCC ACC

L   S   C   R   A   S   Q   S   V   S   S   Y   L   A   W   Y   Q   Q   K   P
 61  CTC TCC TGC AGG GCC AGT CAG AGT GTT AGC AGA TAC TTA GCC TGG TAC CAA CAG AAA CCT

G   Q   A   P   R   L   L   I   Y   D   A   S   N   R   A   T   G   I   P   A
121  GGC CAG GCT CCC AGG CTC CTC ATC TAT GAT GCA TCC AAC AGG GCC ACT GGC ATC CCA GCC

R   F   S   G   S   G   S   G   T   D   F   T   L   T   I   S   S   L   E   P
181  AGG TTC AGT GGC AGT GGG TCT GGG ACA GAC TTC ACT CTC ACC ATC AGC AGC CTA GAG CCT

E   D   F   A   V   Y   Y   C   Q   Q   R   S   N   W   P   R   T   F   G   Q
241  GAA GAT TTT GCA GTT TAT TAC TGT CAG CAG CGT AGC AAC TGG CCT CGG ACG TTC GGC CAA

G   T   K   V   E   I   K   (SEQ ID NO:8)
301  GGG ACC AAG GTG GAA ATC AAA (SEQ ID NO:7)
```

FIG. 2A

```
      M   G   W   S   C   I   I   L   F   L   V   A   T   A   T   G   V   H   S   Q
  1   ATG GGA TGG TCA TGT ATC ATC CTT TTT CTG GTA GCA ACT GCA ACT GGA GTA CAT TCA CAG

V   Q   L   V   Q   S   G   P   E   V   K   K   S   G   S   S   V   K   V   S
 61   GTC CAG CTG GTG CAG TCT GGG CCT GAG GTG AAG AAG TCT GGG TCC TCG GTG AAG GTC TCC

C   K   A   S   G   G   T   F   S   S   D   A   I   T   W   V   R   Q   A   P
121   TGC AAG GCT TCT GGA GGC ACC TTC AGC AGC GAT GCT ATC ACC TGG GTG CGA CAG GCC CCT

G   Q   G   L   E   W   M   G   G   I   I   P   I   L   G   M   A   N   Y   A
181   GGA CAA GGG CTT GAG TGG ATG GGA GGG ATC ATC CCT ATC CTT GGT ATG GCA AAC TAC GCA

Q   K   F   Q   G   R   V   T   I   T   A   D   K   S   T   N   T   A   Y   M
241   CAG AAG TTC CAG GGC AGA GTC ACG ATT ACC GCG GAC AAA TCC ACG AAC ACA GCC TAC ATG

E   L   S   S   L   R   S   E   D   T   A   V   Y   F   C   A   R   V   A   D
301   GAG CTG AGC AGC CTG AGA TCT GAG GAC ACG GCC GTG TAT TTT TGT GCG AGA GTG GCC GAT

Y   Y   G   L   Y   T   Y   W   Y   F   D   L   W   G   R   G   T   L   V
361   TAC TAT GGT TTG TAC ACT TAC TGG TAC TTC GAT CTC TGG GGC CGT GGC ACC CTG GTC

T   V   S   S   A   S   T   K   G   P   S   V   F   P   L   A   P   S   S   K
421   ACT GTC TCC TCA GCT AGC ACC AAG GGC CCA TCG GTC TTC CCC CTG GCA CCC TCC TCC AAG

S   T   S   G   G   T   A   A   L   G   C   L   V   K   D   Y   F   P   E   P
481   AGC ACC TCT GGG GGC ACA GCG GCC CTG GGC TGC CTG GTC AAG GAC TAC TTC CCC GAA CCG
```

FIG. 2B

| Pos | 1 | 2 | 3 | 4 | 5 | 6 | 7 | 8 | 9 | 10 |
|-----|---|---|---|---|---|---|---|---|---|----|
| 541 | V GTG | T ACG | V GTG | S TCG | W TGG | N AAC | S TCA | G GGC | A GCC | L CTG |
|     | T ACC | S AGC | G GGC | V GTG | H CAC | T ACC | F TTC | P CCG | A GCT | V GTC |
| 601 | L CTA | Q CAG | S TCC | S TCA | G GGA | L CTC | Y TAC | S TCC | L CTG | S AGC |
|     | S AGC | V GTG | V GTG | T ACC | V GTG | P CCC | S TCC | S AGC | S AGC | L TTG |
| 661 | G GGC | T ACC | Q CAG | T ACC | Y TAC | I ATC | C TGC | N AAC | V GTG | N AAT |
|     | H CAC | K AAG | P CCC | S AGC | N AAC | T ACC | K AAG | V GTG | D GAC | K AAG |
| 721

FIG. 2C

```
      K   T   I   S   K   A   K   G   Q   P   R   E   P   Q   V   Y   T   L   P   P
1081  AAA ACC ATC TCC AAA GCC AAA GGG CAG CCC CGA GAA CCA CAG GTG TAC ACC CTG CCC CCA

S   R   E   E   M   T   K   N   Q   L   T   C   L   V   K   G   F   Y
1141  TCC CGG GAG GAG ATG ACC AAG AAC CAA CTG ACC TGC CTG GTC AAA GGC TTC TAT

P   S   D   I   A   V   E   W   E   S   N   G   Q   P   E   N   N   Y   K   T
1201  CCC AGC GAC ATC GCC GTG GAG TGG GAG AGC AAT GGG CAG CCG GAG AAC AAC TAC AAG ACC

T   P   P   V   L   D   S   D   G   S   F   F   L   Y   S   K   L   T   V   D
1261  ACG CCT CCC GTG CTG GAC TCC GAC GGC TCC TTC TTC CTC TAT TCC AAG CTC ACC GTG GAC

K   S   R   W   Q   Q   G   N   V   F   S   C   S   V   M   H   E   A   L   H
1321  AAG AGC AGG TGG CAG CAG GGG AAC GTC TTC TCA TGC TCC GTG ATG CAT GAG GCT CTG CAC

N   H   Y   T   Q   K   S   L   S   L   S   P   G   K   *    (SEQ ID NO:10)
1381  AAC CAC TAC ACG CAG AAG AGC CTC TCC CTG TCT CCG GGC AAA TGA  (SEQ ID NO:9)
```

FIG. 2D

```
     M   G   W   S   C   I   I   L   F   L   V   A   T   A   T   G   V   H   S   E
  1  ATG GGA TGG TCA TGT ATC ATC CTT TTT CTG GTA GCA ACT GCA ACT GGA GTA CAT TCA GAA

I   V   L   T   Q   S   P   G   T   L   S   L   S   P   G   E   R   A   T   L
 61  ATT GTG TTG ACG CAG TCT CCA GGC ACC CTG TCT TTG TCT CCA GGG GAA AGA GCC ACC CTC

S   C   R   A   S   Q   S   V   S   S   Y   L   A   W   Y   Q   Q   K   P
121  TCC TGC AGG GCC AGT CAG AGT GTT AGC AGC TAC TTA GCC TGG TAC CAG CAG AAA CCT

G   Q   A   P   R   L   L   I   Y   G   A   S   S   W   A   T   G   I   P   D
181  GGC CAG GCT CCC AGG CTC CTC ATC TAT GGT GCA TCC AGC TGG GCC ACT GGC ATC CCA GAC

R   F   S   G   S   G   S   G   T   D   F   T   L   T   I   S   R   L   E   P
241  AGG TTC AGT GGC AGT GGG TCT GGG ACA GAC TTC ACT CTC ACC ATC AGC AGA CTG GAG CCT

E   D   F   A   V   Y   Y   C   Q   Q   Y   T   V   A   P   S   P   L   T   F   G   G
301  GAA GAT TTT GCA GTG TAT TAC TGT CAG CAA TAT GGT AGC TCA CCT CTC ACT TTC GGC GGA

G   T   K   V   E   I   K   R   T   V   A   A   P   S   V   F   I   F   P   P
361  GGG ACC AAG GTG GAG ATC AAA CGA ACT GTG GCT GCA CCA TCT GTC TTC ATC TTC CCG CCA

S   D   E   Q   L   K   S   G   T   A   S   V   V   C   L   L   N   N   F   Y
421  TCT GAT GAG CAG TTG AAA TCT GGA ACT GCC TCT GTT GTG TGC CTG CTG AAT AAC TTC TAT

P   R   E   A   K   V   Q   W   K   V   D   N   A   L   Q   S   G   N   S   Q
481  CCC AGA GAG GCC AAA GTA CAG TGG AAG GTG GAT AAC GCC CTC CAA TCG GGT AAC TCC CAG
```

FIG. 2E

```
     E   S   V   T   E   Q   D   S   K   D   S   T   Y   S   L   S   T   L   T
541  GAG AGT GTC ACA GAG CAG GAC AGC AAG GAC AGC ACC TAC AGC CTC AGC AGC ACC CTG ACG

L   S   K   A   D   Y   E   K   H   K   V   Y   A   C   E   V   T   H   Q   G
601  CTG AGC AAA GCA GAC TAC GAG AAA CAC AAA GTC TAC GCC TGC GAA GTC ACC CAT CAG GGC

L   S   S   P   V   T   K   S   F   N   R   G   E   C   *   (SEQ ID NO:12)
661  CTG AGC TCG CCC GTC ACA AAG AGC TTC AAC AGG GGA GAG TGT TAG (SEQ ID NO:11)
```

FIG. 3A

```
     M   G   W   S   C   I   I   L   F   L   V   A   T   A   T   G   V   H   S   E
1    ATG GGA TGG TCA TGT ATC ATC CTT TTT CTG GTA GCA ACT GCA ACT GGA GTA CAT TCA GAG

V   Q   L   V   Q   S   G   G   G   L   V   Q   P   G   G   S   L   R   L   S
61   GTG CAG CTG GTG GAG TCT GGG GGA GGC TTG GTC CAA CCT GGG GGG TCC CTG AGA CTC TCC

C   A   A   S   G   F   T   F   S   Y   S   M   N   I   K   Q   D   G   S   E   K   Y   Y   V
121  TGT GCA GCC TCT GGA TTC ACC TTT AGT AGT TAT AGT ATG AAT ATA AAG CAA GAT GGA AGT GAG AAA TAC TAT GTG

G   K   G   L   E   W   V   A   N   I   K   Q   D   G   S   E   K   Y   Y   V
181  GGG AAA GGG CTG GAG TGG GTG GCC AAC ATA AAG CAA GAT GGA AGT GAG AAA TAC TAT GTG

D   S   V   K   G   R   F   T   I   S   R   D   N   A   K   N   S   L   N   L
241  GAC TCT GTG AAG GGC CGA TTC ACC ATC TCC AGA GAC AAC GCC AAG AAC TCA CTG AAT CTG

Q   M   N   S   L   R   A   E   D   T   A   V   Y   Y   C   T   R   D   G   Y
301  CAA ATG AAC AGT CTG AGA GCC GAG GAC ACG GCT GTG TAT TAT TGT ACG AGG GAT GGC TAT

S   S   G   R   H   Y   G   M   D   V   W   G   Q   G   T   T   V   T   V   S
361  AGT TCG GGG AGA CAC TAC GGT ATG GAC GTC TGG GGC CAA GGG ACC ACG GTC ATC GTC TCC

S   A   S   T   K   G   P   S   V   F   P   L   A   P   S   S   K   S   T   S
421  TCA GCT AGC ACC AAG GGC CCA TCG GTC TTC CCC CTG GCA CCC TCC TCC AAG AGC ACC TCT

G   G   T   A   A   L   G   C   L   V   K   D   Y   F   P   E   P   V   T   V
481  GGG GGC ACA GCG GCC CTG GGC TGC CTG GTC AAG GAC TAC TTC CCC GAA CCG GTG ACG GTG

S   W   N   S   G   A   L   T   S   G   V   H   T   F   P   A   V   L   Q   S
541  TCG TGG AAC TCA GGC GCC CTG ACC AGC GGC GTG CAC ACC TTC CCG GCT GTC CTA CAG TCC
```

FIG. 3B

| | | | | | | | | | | | | | | | | | | | | |
|---|---|---|---|---|---|---|---|---|---|---|---|---|---|---|---|---|---|---|---|---|
| 601 | S TCA | G GGA | L CTC | Y TAC | S TCC | L CTC | S AGC | S AGC | V GTG | V GTG | T ACC | V GTG | P CCC | S TCC | S AGC | S AGC | L TTG | G GGC | T ACC | Q CAG |
| 661 | T ACC | Y TAC | I ATC | C TGC | N AAC | V GTG | N AAT | H CAC | K AAG | P CCC | S AGC | N AAC | T ACC | K AAG | V GTG | D GAC | K AAG | R AGA | V GTT | E GAG |
| 721 | P CCC | K AAA | S TCT | C TGT | D GAC | K AAA | T ACT | H CAC | T ACA | C TGC | P CCA | P CCG | C TGC | P CCA | A GCA | P CCT | E GAA | L CTC | L CTG | G GGG |
| 781 | G GGA | P CCG | S TCA | V GTC | F TTC | L CTC | F TTC | P CCC | P CCA | K AAA | P CCC | K AAG | D GAC | T ACC | L CTC | M ATG | I ATC | S TCC | R CGG | T ACC |
| 841 | P CCT | E GAG | V GTC | T ACA | C TGC | V GTG | V GTG | V GTG | D GAC | V GTG | S AGC | H CAC | E GAA | D GAC | P CCT | E GAG | V GTC | K AAG | F TTC | N AAC |
| 901 | W TGG | Y TAT | V GTG | D GAC | G GGC | V GTG | E GAG | V GTG | H CAT | N AAT | A GCC | K AAG | T ACA | K AAG | P CCG | R CGG | E GAG | E GAG | Q CAG | Y TAC |
| 961 | N AAC | S AGC | T ACG | Y TAC | R CGT | V GTG | V GTC | S AGC | V GTC | L CTC | T ACC | V GTC | L CTG | H CAC | Q CAA | D GAC | W TGG | L CTG | N AAT | G GGC |
| 1021 | K AAG | E GAG | Y TAC | K AAG | C TGC | K AAG | V GTC | S TCC | N AAC | K AAA | A GCC | L CTC | P CCA | A GCC | P CCC | I ATC | E GAG | K AAA | T ACC | I ATC |
| 1081 | S TCC | K AAA | A GCC | K AAA | G GGG | Q CAG | P CCC | R CGA | E GAA | P CCA | Q CAG | V GTG | Y TAC | T ACC | L CTG | P CCC | P CCA | S TCC | R CGG | E GAG |

FIG. 3C

```
         E   M   T   K   N   Q   V   S   L   T   C   L   V   K   G   F   Y   P   S   D
1141    GAG ATG ACC AAG AAC CAA GTC AGC CTG ACC TGC CTG GTC AAA GGC TTC TAT CCC AGC GAC

I   A   V   E   W   E   S   N   G   Q   P   E   N   N   Y   K   T   T   P   P
1201    ATC GCC GTG GAG TGG GAG AGC AAT GGG CAG CCG GAG AAC AAC TAC AAG ACC ACG CCT CCC

V   L   D   S   D   G   S   F   F   L   Y   S   K   L   T   V   D   K   S   R
1261    GTG CTG GAC TCC GAC GGC TCC TTC TTC CTC TAT AGC AAG CTC ACC GTG GAC AAG AGC AGG

W   Q   Q   G   N   V   F   S   C   S   V   M   H   E   A   L   H   N   H   Y
1321    TGG CAG CAG GGG AAC GTC TTC TCA TGC TCC GTG ATG CAT GAG GCT CTG CAC AAC CAC TAC

T   Q   K   S   L   S   L   S   P   G   K   *   (SEQ ID NO: 14)
1381    ACG CAG AAG AGC CTC TCC CTG TCT CCG GGC AAA TGA (SEQ ID NO:13)
```

FIG. 3D

```
      M   G   W   S   C   I   I   L   F   L   V   A   T   A   T   G   V   H   S   E
  1   ATG GGA TGG TCA TGT ATC ATC CTT TTT CTG GTA GCA ACT GCA ACT GGA GTA CAT TCA GAA

I   V   L   T   Q   S   P   A   T   L   S   L   S   P   G   E   R   A   T   L
 61   ATT GTG TTG ACA CAG TCT CCA GCC ACC CTG TCT TTG TCT CCA GGG GAA AGA GCC ACC CTC

S   C   R   A   S   Q   S   V   S   R   Y   L   A   W   Y   Q   Q   K   P   G
121   TCC TGC AGG GCC AGT CAG AGT GTT AGC AGA TAC TTA GCC TGG TAC CAA CAG AAA CCT GGC

Q   A   P   R   L   L   I   Y   D   A   S   N   R   A   T   G   I   P   A   R
181   CAG GCT CCC AGG CTC CTC ATC TAT GAT GCA TCC AAC AGG GCC ACT GGC ATC CCA GCC AGG

F   S   G   S   G   S   G   T   D   F   T   L   T   I   S   S   L   E   P   E
241   TTC AGT GGC AGT GGG TCT GGG ACA GAC TTC ACT CTC ACC ATC AGC AGC CTA GAG CCT GAA

D   F   A   V   Y   Y   C   Q   Q   R   S   N   W   P   R   T   F   G   Q   G
301   GAT TTT GCA GTT TAT TAC TGT CAG CAG CGT AGC AAC TGG CCT CGG ACG TTC GGC CAA GGG

T   K   V   E   I   K   R   T   V   A   A   P   S   V   F   I   F   P   P   S
361   ACC AAG GTG GAA ATC AAA CGA ACT GTG GCT GCA CCA TCT GTC TTC ATC TTC CCG CCA TCT

D   E   Q   L   K   S   G   T   A   S   V   V   C   L   L   N   N   F   Y   P
421   GAT GAG CAG TTG AAA TCT GGA ACT GCC TCT GTT GTG TGC CTG CTG AAT AAC TTC TAT CCC

R   E   A   K   V   Q   W   K   V   D   N   A   L   Q   S   G   N   S   Q   E
481   AGA GAG GCC AAA GTA CAG TGG AAG GTG GAT AAC GCC CTC CAA TCG GGT AAC TCC CAG GAG

S   V   T   E   Q   D   S   K   D   S   T   Y   S   L   S   S   T   L   T   L
541   AGT GTC ACA GAG CAG GAC AGC AAG GAC AGC ACC TAC AGC CTC AGC AGC ACC CTG ACG CTG
```

FIG. 3E

```
    S   K   A   D   Y   E   K   H   K   V   Y   A   C   E   V   T   H   Q   G   L
601 AGC AAA GCA GAC TAC GAG AAA CAC AAA GTC TAC GCC TGC GAA GTC ACC CAT CAG GGC CTG

S   S   P   V   T   K   S   F   N   R   G   E   C   *   (SEQ ID NO:16)
661 AGC TCG CCC GTC ACA AAG AGC TTC AAC AGG GGA GAG TGT TAG (SEQ ID NO:15)
```

Cell-based phosphorylation assay (NIH3T3-RON)

Cell-based phosphorylation assay (H-292)

FIG 6C(1)
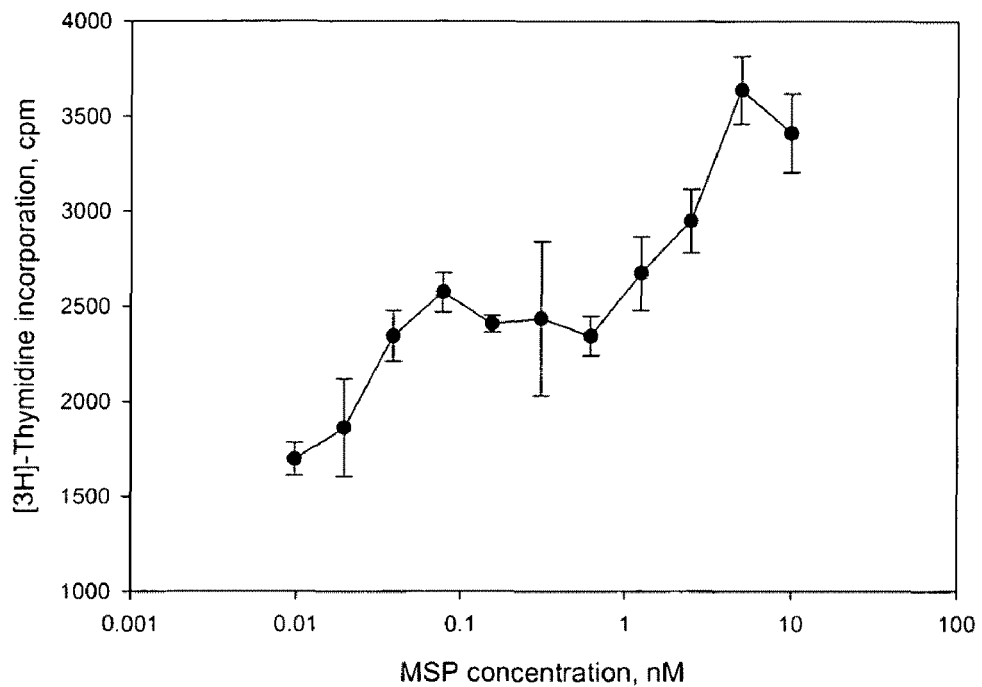
FIG 6C(2)
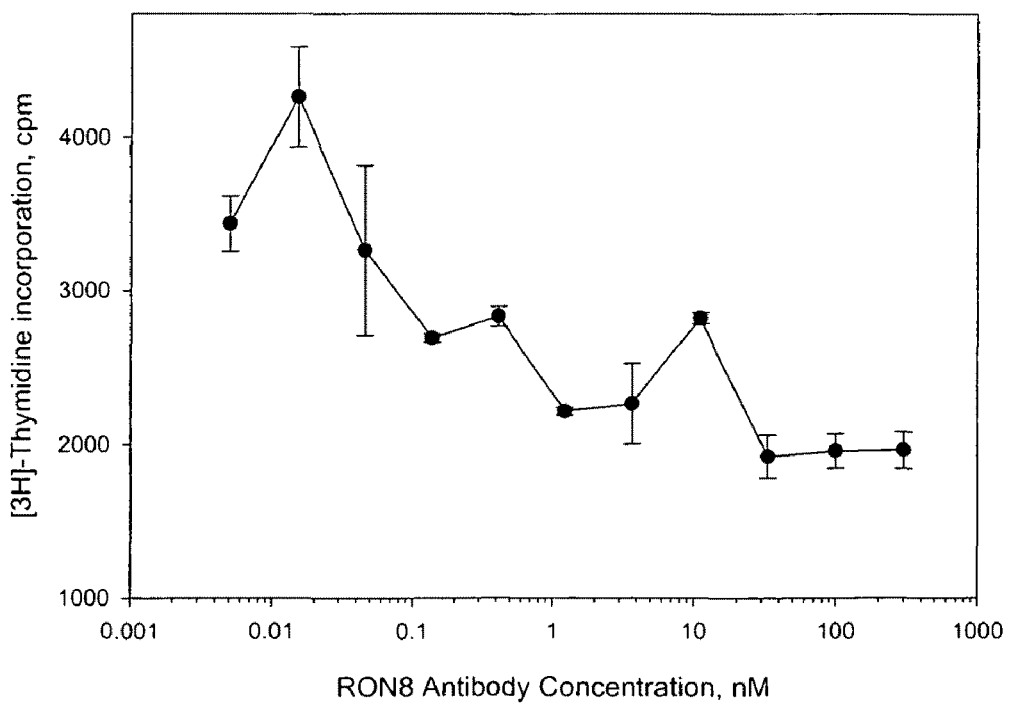

SEQUENCE LISTING

```
<160> NUMBER OF SEQ ID NOS: 51

<210> SEQ ID NO 1
<211> LENGTH: 375
<212> TYPE: DNA
<213> ORGANISM: Homo sapiens

<400> SEQUENCE: 1
caggtccagc tggtgcagtc tgggcctgag gtgaagaagt ctgggtcctc ggtgaaggtc      60
tcctgcaagg cttctggagg caccttcagc agcgatgcta tcacctgggt gcgacaggcc     120
cctggacaag ggcttgagtg gatgggaggg atcatccctc tccttggtat ggcaaactac     180
gcacagaagt tccagggcag agtcacgatt accgcggaca atccacgaa cacagcctac     240
```

```
atggagctga gcagcctgag atctgaggac acggccgtgt attttgtgc gagagtggcc    300 gattactatg gtttggggac ttactactgg tacttcgatc tctggggccg tggcaccctg    360
gtcactgtct cctca                                                     375
```

<210> SEQ ID NO 2
<211> LENGTH: 125
<212> TYPE: PRT
<213> ORGANISM: Homo sapiens

<400> SEQUENCE: 2

```
Gln Val Gln Leu Val Gln Ser Gly Pro Glu Val Lys Lys Ser Gly Ser
1               5                   10                  15

Ser Val Lys Val Ser Cys Lys Ala Ser Gly Gly Thr Phe Ser Ser Asp
            20                  25                  30

Ala Ile Thr Trp Val Arg Gln Ala Pro Gly Gln Gly Leu Glu Trp Met
        35                  40                  45

Gly Gly Ile Ile Pro Ile Leu Gly Met Ala Asn Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Val Ala Asp Tyr Tyr Gly Leu Gly Thr Tyr Tyr Trp Tyr Phe
            100                 105                 110

Asp Leu Trp Gly Arg Gly Thr Leu Val Thr Val Ser Ser
        115                 120                 125
```

<210> SEQ ID NO 3
<211> LENGTH: 324
<212> TYPE: DNA
<213> ORGANISM: Homo sapiens

<400> SEQUENCE: 3

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gctgggccac tggcatccca   180
gacaggttca gtggcagtgg gtctgggaca gacttcactc tcaccatcag cagactggag   240
cctgaagatt ttgcagtgta ttactgtcag caatatggta gctcacctct cactttcggc   300
ggagggacca aggtggagat caaa                                          324
```

<210> SEQ ID NO 4
<211> LENGTH: 108
<212> TYPE: PRT
<213> ORGANISM: Homo sapiens

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 5
<211> LENGTH: 366
<212> TYPE: DNA
<213> ORGANISM: Homo sapiens

<400> SEQUENCE: 5
gaggtgcagc tggtggagtc tgggggaggc ttggtccaac ctggggggtc cctgagactc      60
tcctgtgcag cctctggatt cacctttagt agttatttaa tgacctgggt ccgccaggct     120
ccagggaaag gctggagtg gtggccaac ataaagcaag atggaagtga aaatactat       180 gtggactctg tgaagggccg attcaccatc tccagagaca acgccaagaa ctcactgaat     240
ctgcaaatga acagtctgag agccgaggac acggctgtgt attattgtac gagggatggc     300
tatagttcgg ggagacacta cggtatggac gtctggggcc aagggaccac ggtcatcgtc     360
tcctca                                                                366

<210> SEQ ID NO 6
<211> LENGTH: 122
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Thr Arg Asp Gly Tyr Ser Ser Gly Arg His Tyr Gly Met Asp Val Trp
            100                 105                 110

Gly Gln Gly Thr Thr Val Ile Val Ser Ser
        115                 120

<210> SEQ ID NO 7
<211> LENGTH: 321
<212> TYPE: DNA
<213> ORGANISM: Homo sapiens

<400> SEQUENCE: 7
gaaattgtgt tgacacagtc tccagccacc ctgtctttgt ctccagggga aagagccacc      60
ctctcctgca gggccagtca gagtgttagc agatacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctcggac gttcggccaa     300
gggaccaagg tggaaatcaa a                                               321

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 9
<211> LENGTH: 1425
<212> TYPE: DNA
<213> ORGANISM: Homo sapiens

<400> SEQUENCE: 9
atgggatggt catgtatcat ccttttttctg gtagcaactg caactggagt acattcacag      60
gtccagctgg tgcagtctgg gcctgaggtg aagaagtctg gtcctcggt gaaggtctcc      120
tgcaaggctt ctggaggcac cttcagcagc gatgctatca cctgggtgcg acaggcccct      180
ggacaagggc ttgagtggat gggagggatc atccctatcc ttggtatggc aaactacgca      240
cagaagttcc agggcagagt cacgattacc gcggacaaat ccacgaacac agcctacatg      300
gagctgagca gcctgagatc tgaggacacg gccgtgtatt tttgtgcgag agtggccgat      360
tactatggtt tggggactta ctactggtac ttcgatctct ggggccgtgg caccctggtc      420
actgtctcct cagctagcac caagggccca tcggtcttcc ccctggcacc ctcctccaag      480
agcacctctg ggggcacagc ggccctgggc tgcctggtca aggactactt ccccgaaccg      540
gtgacggtgt cgtggaactc aggcgccctg accagcggcg tgcacacctt cccggctgtc      600
ctacagtcct caggactcta ctccctcagc agcgtggtga ccgtgccctc agcagcttg      660
ggcacccaga cctacatctg caacgtgaat cacaagccca gcaacaccaa ggtggacaag      720
agagttgagc ccaaatcttg tgacaaaact cacacatgcc caccgtgccc agcacctgaa      780
ctcctggggg gaccgtcagt cttcctcttc ccccccaaaac ccaaggacac cctcatgatc      840
tcccggaccc ctgaggtcac atgcgtggtg gtggacgtga gccacgaaga ccctgaggtc      900
aagttcaact ggtatgtgga cggcgtggag gtgcataatg ccaagacaaa gccgcgggag      960
gagcagtaca acagcacgta ccgtgtggtc agcgtcctca ccgtcctgca ccaagactgg     1020
ctgaatggca aggagtacaa gtgcaaggtc tccaacaaag ccctcccagc ccccatcgag     1080
aaaaccatct ccaaagccaa agggcagccc cgagaaccac aggtgtacac cctgcccccca     1140
tcccgggagg agatgaccaa gaaccaagtc agcctgacct gcctggtcaa aggcttctat     1200
cccagcgaca tcgccgtgga gtgggagagc aatgggcagc cggagaacaa ctacaagacc     1260

```
acgcctcccg tgctggactc cgacggctcc ttcttcctct attccaagct caccgtggac    1320
aagagcaggt ggcagcaggg gaacgtcttc tcatgctccg tgatgcatga ggctctgcac    1380
aaccactaca cgcagaagag cctctccctg tctccgggca aatga                    1425
```

```
<210> SEQ ID NO 10
<211> LENGTH: 474
<212> TYPE: PRT
<213> ORGANISM: Homo sapiens

<400> SEQUENCE: 10

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Ser Gly Ser Ser Val Lys Val Ser Cys Lys Ala Ser Gly Gly Thr Phe
        35                  40                  45

Ser Ser Asp Ala Ile Thr Trp Val Arg Gln Ala Pro Gly Gln Gly Leu
    50                  55                  60

Glu Trp Met Gly Gly Ile Ile Pro Ile Leu Gly Met Ala Asn Tyr Ala
65                  70                  75                  80

Gln Lys Phe Gln Gly Arg Val Thr Ile Thr Ala Asp Lys Ser Thr Asn
                85                  90                  95

Thr Ala Tyr Met Glu Leu Ser Ser Leu Arg Ser Glu Asp Thr Ala Val
            100                 105                 110

Tyr Phe Cys Ala Arg Val Ala Asp Tyr Tyr Gly Leu Gly Thr Tyr Tyr
        115                 120                 125

Trp Tyr Phe Asp Leu Trp Gly Arg Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350
```

```
Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 11
<211> LENGTH: 705
<212> TYPE: DNA
<213> ORGANISM: Homo sapiens

<400> SEQUENCE: 11

```
atgggatggt catgtatcat ccttttttctg gtagcaactg caactggagt acattcagaa      60
attgtgttga cgcagtctcc aggcaccctg tctttgtctc caggggaaag agccaccctc     120
tcctgcaggg ccagtcagag tgttagcagc agctacttag cctggtacca gcagaaacct     180
ggccaggctc ccaggctcct catctatggt gcatccagct gggccactgg catcccagac     240
aggttcagtg gcagtgggtc tgggacagac ttcactctca ccatcagcag actggagcct     300
gaagattttg cagtgtatta ctgtcagcaa tatggtagct cacctctcac tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttag                     705
```

<210> SEQ ID NO 12
<211> LENGTH: 234
<212> TYPE: PRT
<213> ORGANISM: Homo sapiens

<400> SEQUENCE: 12

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp Tyr Gln Gln Lys Pro Gly Gln Ala Pro
    50                  55                  60

Arg Leu Leu Ile Tyr Gly Ala Ser Ser Trp Ala Thr Gly Ile Pro Asp
65                  70                  75                  80

Arg Phe Ser Gly Ser Gly Ser Gly Thr Asp Phe Thr Leu Thr Ile Ser
```

```
                    85                  90                  95
Arg Leu Glu Pro Glu Asp Phe Ala Val Tyr Tyr Cys Gln Gln Tyr Gly
            100                 105                 110

Ser Ser Pro Leu Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 13
<211> LENGTH: 1416
<212> TYPE: DNA
<213> ORGANISM: Homo sapiens

<400> SEQUENCE: 13
atgggatggt catgtatcat ccttttttctg gtagcaactg caactggagt acattcagag     60
gtgcagctgg tggagtctgg gggaggcttg gtccaacctg ggggtccct gagactctcc     120 tgtgcagcct ctggattcac ctttagtagt tatttaatga cctgggtccg ccaggctcca     180
gggaaagggc tggagtgggt ggccaacata aagcaagatg gaagtgagaa atactatgtg     240
gactctgtga agggccgatt caccatctcc agagacaacg ccaagaactc actgaatctg     300
caaatgaaca gtctgagagc cgaggacacg gctgtgtatt attgtacgag ggatggctat     360
agttcgggga gactacggg tatggacgtc tggggccaag ggaccacggt catcgtctcc     420
tcagctagca ccaagggccc atcggtcttc cccctggcac cctcctccaa gagcacctct     480
gggggcacag cggccctggg ctgcctggtc aaggactact ccccgaacc ggtgacggtg     540 tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gagagttgag     720
cccaaatctt gtgacaaaac tcacacatgc ccaccgtgcc cagcacctga actcctgggg     780
ggaccgtcag tcttcctctt cccccaaaaa cccaaggaca ccctcatgat ctcccggacc     840
cctgaggtca catgcgtggt ggtggacgtg agccacgaag accctgaggt caagttcaac     900
tggtatgtgg acggcgtgga ggtgcataat gccaagacaa agccgcggga ggagcagtac     960
aacagcacgt accgtgtggt cagcgtcctc accgtcctgc accaagactg gctgaatggc     1020
aaggagtaca agtgcaaggt ctccaacaaa gccctcccag cccccatcga gaaaaccatc     1080
tccaaagcca aagggcagcc ccgagaacca caggtgtaca ccctgccccc atcccgggag     1140
gagatgacca gaaccaagt cagcctgacc tgcctggtca aaggcttcta tcccagcgac     1200
atcgccgtgg agtgggagag caatgggcag ccggagaaca actacaagac cacgcctccc     1260
gtgctggact ccgacggctc cttcttcctc tattccaagc tcaccgtgga caagagcagg     1320
```

```
tggcagcagg ggaacgtctt ctcatgctcc gtgatgcatg aggctctgca caaccactac    1380
acgcagaaga gcctctccct gtctccgggc aaatga                              1416
```

<210> SEQ ID NO 14
<211> LENGTH: 471
<212> TYPE: PRT
<213> ORGANISM: Homo sapiens

<400> SEQUENCE: 14

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Leu Met Thr Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Asn Leu Gln Met Asn Ser Leu Arg Ala Glu Asp Thr Ala Val
            100                 105                 110

Tyr Tyr Cys Thr Arg Asp Gly Tyr Ser Ser Gly Arg His Tyr Gly Met
        115                 120                 125

Asp Val Trp Gly Gln Gly Thr Thr Val Ile Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
```

```
                355                 360                 365
Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 15
<211> LENGTH: 702
<212> TYPE: DNA
<213> ORGANISM: Homo sapiens

<400> SEQUENCE: 15
atgggatggt catgtatcat ccttttttctg gtagcaactg caactggagt acattcagaa      60
attgtgttga cacagtctcc agccaccctg tctttgtctc caggggaaag agccaccctc     120
tcctgcaggg ccagtcagag tgttagcaga tacttagcct ggtaccaaca gaaacctggc     180
caggctccca ggctcctcat ctatgatgca tccaacaggg ccactggcat cccagccagg     240
ttcagtggca gtgggtctgg gacagacttc actctcacca tcagcagcct agagcctgaa     300
gattttgcag tttattactg tcagcagcgt agcaactggc tcggacgtt cggccaaggg      360 accaaggtgg aaatcaaacg aactgtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag      540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702

<210> SEQ ID NO 16
<211> LENGTH: 233
<212> TYPE: PRT
<213> ORGANISM: Homo sapiens

<400> SEQUENCE: 16

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
                20                  25                  30

Ser Pro Gly Glu Arg Ala Thr Leu Ser Cys Arg Ala Ser Gln Ser Val
            35                  40                  45

Ser Arg Tyr Leu Ala Trp Tyr Gln Gln Lys Pro Gly Gln Ala Pro Arg
        50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95
```

Leu Glu Pro Glu Asp Phe Ala Val Tyr Tyr Cys Gln Gln Arg Ser Asn
            100                 105                 110

Trp Pro Arg Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 17
<211> LENGTH: 10
<212> TYPE: PRT
<213> ORGANISM: Homo sapiens

<400> SEQUENCE: 17

Gly Gly Thr Phe Ser Ser Asp Ala Ile Thr
1               5                   10

<210> SEQ ID NO 18
<211> LENGTH: 30
<212> TYPE: DNA
<213> ORGANISM: Homo sapiens

<400> SEQUENCE: 18
ggaggcacct tcagcagcga tgctatcacc                                    30

<210> SEQ ID NO 19
<211> LENGTH: 17
<212> TYPE: PRT
<213> ORGANISM: Homo sapiens

<400> SEQUENCE: 19

Gly Ile Ile Pro Ile Leu Gly Met Ala Asn Tyr Ala Gln Lys Phe Gln
1               5                   10                  15

Gly

<210> SEQ ID NO 20
<211> LENGTH: 51
<212> TYPE: DNA
<213> ORGANISM: Homo sapiens

<400> SEQUENCE: 20
gggatcatcc ctatccttgg tatggcaaac tacgcacaga agttccaggg c            51

<210> SEQ ID NO 21
<211> LENGTH: 16
<212> TYPE: PRT
<213> ORGANISM: Homo sapiens

<400> SEQUENCE: 21

```
Val Ala Asp Tyr Tyr Gly Leu Gly Thr Tyr Tyr Trp Tyr Phe Asp Leu
1               5                   10                  15
```

<210> SEQ ID NO 22
<211> LENGTH: 48
<212> TYPE: DNA
<213> ORGANISM: Homo sapiens

<400> SEQUENCE: 22
gtggccgatt actatggttt ggggacttac tactggtact tcgatctc         48

<210> SEQ ID NO 23
<211> LENGTH: 12
<212> TYPE: PRT
<213> ORGANISM: Homo sapiens

<400> SEQUENCE: 23

```
Arg Ala Ser Gln Ser Val Ser Ser Ser Tyr Leu Ala
1               5                   10
```

<210> SEQ ID NO 24
<211> LENGTH: 36
<212> TYPE: DNA
<213> ORGANISM: Homo sapiens

<400> SEQUENCE: 24
agggccagtc agagtgttag cagcagctac ttagcc         36

<210> SEQ ID NO 25
<211> LENGTH: 7
<212> TYPE: PRT
<213> ORGANISM: Homo sapiens

<400> SEQUENCE: 25

```
Gly Ala Ser Ser Trp Ala Thr
1               5
```

<210> SEQ ID NO 26
<211> LENGTH: 21
<212> TYPE: DNA
<213> ORGANISM: Homo sapiens

<400> SEQUENCE: 26
ggtgcatcca gctgggccac t         21

<210> SEQ ID NO 27
<211> LENGTH: 9
<212> TYPE: PRT
<213> ORGANISM: Homo sapiens

<400> SEQUENCE: 27

```
Gln Gln Tyr Gly Ser Ser Pro Leu Thr
1               5
```

<210> SEQ ID NO 28
<211> LENGTH: 27
<212> TYPE: DNA
<213> ORGANISM: Homo sapiens

<400> SEQUENCE: 28
cagcaatatg gtagctcacc tctcact         27

<210> SEQ ID NO 29
<211> LENGTH: 10
<212> TYPE: PRT

```
<213> ORGANISM: Homo sapiens

<400> SEQUENCE: 29

Gly Phe Thr Phe Ser Ser Tyr Leu Met Thr
1               5                   10

<210> SEQ ID NO 30
<211> LENGTH: 30
<212> TYPE: DNA
<213> ORGANISM: Homo sapiens

<400> SEQUENCE: 30
ggattcacct ttagtagtta tttaatgacc                                    30

<210> SEQ ID NO 31
<211> LENGTH: 17
<212> TYPE: PRT
<213> ORGANISM: Homo sapiens

<400> SEQUENCE: 31

Asn Ile Lys Gln Asp Gly Ser Glu Lys Tyr Tyr Val Asp Ser Val Lys
1               5                   10                  15

Gly

<210> SEQ ID NO 32
<211> LENGTH: 51
<212> TYPE: DNA
<213> ORGANISM: Homo sapiens

<400> SEQUENCE: 32
aacataaagc aagatggaag tgagaaatac tatgtggact ctgtgaaggg c            51

<210> SEQ ID NO 33
<211> LENGTH: 13
<212> TYPE: PRT
<213> ORGANISM: Homo sapiens

<400> SEQUENCE: 33

Asp Gly Tyr Ser Ser Gly Arg His Tyr Gly Met Asp Val
1               5                   10

<210> SEQ ID NO 34
<211> LENGTH: 39
<212> TYPE: DNA
<213> ORGANISM: Homo sapiens

<400> SEQUENCE: 34
gatggctata gttcggggag acactacggt atggacgtc                          39

<210> SEQ ID NO 35
<211> LENGTH: 11
<212> TYPE: PRT
<213> ORGANISM: Homo sapiens

<400> SEQUENCE: 35

Arg Ala Ser Gln Ser Val Ser Arg Tyr Leu Ala
1               5                   10

<210> SEQ ID NO 36
<211> LENGTH: 33
<212> TYPE: DNA
<213> ORGANISM: Homo sapiens

<400> SEQUENCE: 36
```

```
agggccagtc agagtgttag cagatactta gcc                                    33
```

<210> SEQ ID NO 37
<211> LENGTH: 7
<212> TYPE: PRT
<213> ORGANISM: Homo sapiens

<400> SEQUENCE: 37

Asp Ala Ser Asn Arg Ala Thr
1               5

<210> SEQ ID NO 38
<211> LENGTH: 21
<212> TYPE: DNA
<213> ORGANISM: Homo sapiens

<400> SEQUENCE: 38

```
gatgcatcca acagggccac t                                                 21
```

<210> SEQ ID NO 39
<211> LENGTH: 9
<212> TYPE: PRT
<213> ORGANISM: Homo sapiens

<400> SEQUENCE: 39

Gln Gln Arg Ser Asn Trp Pro Arg Thr
1               5

<210> SEQ ID NO 40
<211> LENGTH: 27
<212> TYPE: DNA
<213> ORGANISM: Homo sapiens

<400> SEQUENCE: 40

```
cagcagcgta gcaactggcc tcggacg                                           27
```

<210> SEQ ID NO 41
<211> LENGTH: 5
<212> TYPE: PRT
<213> ORGANISM: Homo sapiens

<400> SEQUENCE: 41

Ser Tyr Ala Ile Ser
1               5

<210> SEQ ID NO 42
<211> LENGTH: 17
<212> TYPE: PRT
<213> ORGANISM: Homo sapiens

<400> SEQUENCE: 42

Gly Ile Ile Pro Ile Phe Gly Thr Ala Asn Tyr Ala Gln Lys Phe Gln
1               5                   10                  15

Gly

<210> SEQ ID NO 43
<211> LENGTH: 21
<212> TYPE: PRT
<213> ORGANISM: Homo sapiens

<400> SEQUENCE: 43

Ala Pro Leu Arg Phe Leu Glu Trp Ser Thr Gln Asp His Tyr Tyr Tyr
1               5                   10                  15

Tyr Tyr Met Asp Val

```
<210> SEQ ID NO 44
<211> LENGTH: 11
<212> TYPE: PRT
<213> ORGANISM: Homo sapiens

<400> SEQUENCE: 44

Gln Gly Asp Ser Leu Arg Ser Tyr Tyr Ala Ser
1               5                   10

<210> SEQ ID NO 45
<211> LENGTH: 7
<212> TYPE: PRT
<213> ORGANISM: Homo sapiens

<400> SEQUENCE: 45

Gly Lys Asn Asn Arg Pro Ser
1               5

<210> SEQ ID NO 46
<211> LENGTH: 11
<212> TYPE: PRT
<213> ORGANISM: Homo sapiens

<400> SEQUENCE: 46

Asn Ser Arg Asp Asn Ser Asp Asn Arg Leu Ile
1               5                   10

<210> SEQ ID NO 47
<211> LENGTH: 11
<212> TYPE: PRT
<213> ORGANISM: Homo sapiens

<400> SEQUENCE: 47

Gln Gly Asp Ser Leu Arg Ser Tyr Tyr Ala Thr
1               5                   10

<210> SEQ ID NO 48
<211> LENGTH: 7
<212> TYPE: PRT
<213> ORGANISM: Homo sapiens

<400> SEQUENCE: 48

Gly Glu Asn Lys Arg Pro Ser
1               5

<210> SEQ ID NO 49
<211> LENGTH: 11
<212> TYPE: PRT
<213> ORGANISM: Homo sapiens

<400> SEQUENCE: 49

Lys Ser Arg Asp Gly Ser Gly Gln His Leu Val
1               5                   10

<210> SEQ ID NO 50
<211> LENGTH: 452
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Leu Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Thr Arg Asp Gly Tyr Ser Ser Gly Arg His Tyr Gly Met Asp Val Trp
            100                 105                 110

Gly Gln Gly Thr Thr Val Ile Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445
```

-continued

```
<210> SEQ ID NO 51
<211> LENGTH: 214
<212> TYPE: PRT
<213> ORGANISM: Homo sapiens

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

US 7,947,811 B2

ANTIBODIES THAT BIND SPECIFICALLY TO HUMAN RON PROTEIN

CROSS-REFERENCE TO RELATED APPLICATIONS

This application claims the benefit of U.S. Provisional Application U.S. Ser. No. 60/989,558 filed Nov. 21, 2007 the entire contents of which are hereby incorporated by reference.

FIELD OF THE INVENTION

The present invention pertains to methods and compositions for inhibiting the human Macrophage-Stimulating Protein Receptor ("MSP-R" or "RON" (receptor d'origine nantais)). The present invention further provides methods for treatment of tumors and other diseases in a mammal comprising administration of antibodies or antibody fragments specific for RON that inhibit RON activation.

STATEMENT UNDER 37 C.F.R. §1.77(b)(5)

This application contains a Sequence Listing which is filed concurrently herewith in computer readable form on the accompanying compact disc as file name "30040.txt", a 30 KB file created on Oct. 30, 2008, the entire contents of which are hereby incorporated by reference.

BACKGROUND OF THE INVENTION

The Macrophage-Stimulating Protein Receptor, hereinafter also referred to as "RON", belongs to the c-met family of receptor tyrosine kinases. RON is a heterodimeric protein comprised of an extracellular alpha chain and a transmembrane beta chain. RON is first expressed as a single chain precursor, followed by cleavage into the alpha and the beta chains (1). It is believed that the beta chain is required for binding of its ligand, Macrophage-Stimulating Protein ("MSP"; a/k/a HGF-like protein), to the receptor, and the Kringle domains of 2 and 3 of MSP, are required for RON/MSP interaction. See, U.S. Publ. No. 2003/0073656. The extracellular domain of RON is thought to have little homology with the corresponding domains of the c-met family receptors. Indeed, binding of Hepatocyte Growth Factor ("HGF"), which stimulates other receptors in the c-met family, to the RON receptor, does not stimulate tyrosine kinase activity (WO 02/083,047).

RON is thought to have a role in cell migration, shape change and invasion of tissues by tumors (1). An earlier publication, however, reported a limited role for RON for inducing transformation, but described a promotion of invasive growth by RON activation (16).

Mutations, deletions, gene rearrangements and alternative mRNA splicing may cause activation of RON without any ligand binding (1). Variations in the tyrosine kinase domain of RON may play an important role in activation of RON (1). Cloning of RON from various cancer cell lines has shown RON activation due to various defects in the mRNA encoding for RON.

MSP is a member of the kringle-domain plasminogen-related protein family (1). As its name implies, MSP was originally found to stimulate macrophages by a variety of means (for review, see 2, 3). For example, addition of MSP to certain RON-expressing macrophages induced shape changes, chemotaxis, macropinocytosis, phagocytosis and immune mediator production (4, 5, 6). RON was also found to be expressed in epithelial cells such as keratinocytes where MSP was shown to phosphorylate RON and activate a number of signaling pathways that elicited cell adhesion/motility, anti-apoptotic and proliferative responses (7,8). Within the last few years, over-expression of RON has been observed in several epithelial tumors and cell lines (ex. colon (9, 10, 11), lung (12), breast (13)). In a recent study, lung tumors developed in transgenic mice engineered to over-express RON in their lungs (14, 15).

RON is expressed in a variety of human cancer cell lines. An antibody to RON can inhibit activation of the receptor (phosphorylated RON) as well as activation of the downstream signaling molecules: phosphor-MAPK and phosphor-AKT in many of these cancer cell lines. Both of the anti-RON antibodies (RON6 and RON8) exemplified hereinbelow, are shown to significantly retard the ability of several cancer derived cell lines (HT-29 colon, H-292 lung, BxPC3 pancreas, JIMT-1 breast) to form tumors when injected into nude mice. This confirms that inhibition of RON receptor tyrosine kinase negatively influences the proliferation of these cancer cells, and underscores the utility of inhibiting RON in, for example, colon, lung, pancreatic and breast cancers. Using conventional Western blot and flow cytometry procedures, RON has been shown to be expressed in many human cell lines derived from a variety of cancers: colon (HT-29, Colo205, HCT-116, DLD-1, Sw480, Sw620), pancreatic (BXPC-3, CAPAN-2, ASPC-1, HPAF-II, L3.7p1#7, Hs766T), prostate (DU-145, PC-3), stomach (AGS, NCI-N87), lung (A549, H596) liver (HepG2, SNU-182) and breast (JIMT1, DU4475, AU565).

There is a continuing need in the art for developing treatments for various diseases, particularly cancer, based on identifying RON targets, including specific RON epitopes.

SUMMARY OF THE INVENTION

Accordingly, the invention provides for anti-RON antibodies, with substantially higher specific binding than known anti-RON antibodies previously available. The antibodies may be isolated and/or purified. The inventive antibodies are useful for binding to RON, whether encoded by the wild type RON alleles that are typically found in the human population, or variant RON proteins, e.g., those with minor variations or mutations, but that retain RON activity. In one embodiment, the inventive antibody or antibodies are specific for RON, and have a $K_d$ (i.e., equilibrium constant for dissociation of an antigen with an antibody) of about $1 \times 10^{-9}$ $M^{-1}$ or less. In other embodiments, the inventive purified antibody exhibits a $K_d$ that is about $1 \times 10^{-10}$ $M^{-1}$ or about $1 \times 10^{-11}$ $M^{-1}$ or less. In still other embodiments, the inventive antibody, or functional fragment thereof is fully human in nature.

The invention provides, for example, an antibody that specifically binds to a RON protein that comprises a complementarity determining region (CDR) derived from one or more antibody variable domains selected from the group consisting of RON6 VH, RON6 VL, RON8 VH, RON8 VL, and combinations thereof, wherein the RON6 VH CDRs are SEQ ID NO:17, SEQ ID NO:19 and SEQ ID NO:21; the RON6 VL CDRs are SEQ ID NO:23, SEQ ID NO:25 and SEQ ID NO:27; the RON8 VH CDRs are SEQ ID NO:29, SEQ ID NO:31 and SEQ ID NO:33; and the RON8 VL CDRs are SEQ ID NO:35, SEQ ID NO:37 and SEQ ID NO:39. Each included variable domain may contribute three CDRs. The antibody may be, e.g., a monoclonal antibody, single chain, Fab, Fv, diabody or triabody.

In some embodiments the antibody may comprise CDRs derived from at least two antibody variable domains selected from the group consisting of RON6 VH, RON6 VL, RON8 VH, RON8 VL, and combinations thereof. More preferably, the inventive antibody comprises CDRs derived from at least three antibody variable domains selected from the group consisting of RON6 VH, RON6 VL, RON8 VH, RON8 VL, and combinations thereof. In some embodiments, the antibody is RON6 or RON8.

The invention further provides for an isolated nucleic acid encoding the antibody, as well as a recombinant vector comprising the nucleic acid operably linked to one or more control sequences that allow for expression of the nucleic acid in a host cell of choice. Host cells comprising the recombinant vector are also provided.

The invention further provides a method of producing a RON antibody of the present invention comprising culturing a host cell under conditions permitting expression of the antibody, and optionally purifying the produced antibody.

The invention still further provides a pharmaceutical composition comprising the inventive antibody, and a pharmaceutically acceptable carrier. The pharmaceutical compositions may further comprise one or more other therapeutically effective agents.

Kits comprising the RON antibodies of the present invention, alone or in combination with other agents, e.g., chemotherapeutic agents, are contemplated herein.

Methods of using the inventive antibody are also provided, including, e.g., a method of treating cancer, inhibiting angiogenesis, tumor growth, migration, proliferation or invasion of tumor cells that express RON, comprising administering to a mammal an effective amount of the inventive antibody or fragment thereof to inhibit activation of RON. The tumor cells are, for example, tumor cells originating in the colon, pancreas, prostate, stomach, lung, liver, ovary, kidney, breast and brain, or of epithelial or neuroendocrine origin.

The inventive methods further include administering other agents, e.g., a small organic molecule, with the antibody, wherein the other agent may include, but is not limited to, a chemotherapeutic agent, anti-angiogenesis agent or inhibits activation of RON. Optionally, the antibody may be conjugated to the other agent, e.g., to a small organic molecule.

The inventive antibody can be administered with at least one other anticancer treatment, e.g., an anti-angiogenesis agent, FGFR-3 antagonist, a chemotherapeutic agent, radiation, an anti-neoplastic agent, small molecule, or other antibody. For example, the inventive antibody may be administered with at least one additional antibody that inhibits tumors, e.g., an anti-EGFR antibody, such as Erbitux® (Imclone Systems, Inc. NY, N.Y.).

The inventive antibody can target or bind to a wild type RON or a variant RON.

The inventive methods of the present invention further include a method of detecting RON in a sample comprising, contacting said sample with the inventive antibody to obtain specific binding, and detecting such binding.

Also provided is a method of preventing or treating inflammation in a mammal in need thereof, comprising administering to the mammal an effective amount of an antibody of the present invention.

Also provided is a method of preventing or treating disease, e.g., liver, biliary tract, bile ducts and gall bladder disease in a mammal in need thereof, comprising administering to the mammal an effective amount of an antibody of the present invention.

Also provided is a method of inhibiting phosphorylation of RON, MAPK and/or Akt in a mammal in need thereof, comprising administering to the mammal an effective amount of an antibody of the present invention.

With regard to the foregoing methods, in some embodiments the inventive antibody or fragment thereof may be administered to a mammal in a dose of about 1 to about 10 mg/Kg. In other embodiments, the antibody or fragment thereof may be administered at a dose of about 3 to about 8 mg/Kg.

BRIEF DESCRIPTION OF THE FIGURES

FIG. 1A illustrates the DNA (SEQ ID NO:1) and translated sequence (SEQ ID NO:2) of the RON6 VH region, with CDRs shown in singleunderline.

FIG. 1B illustrates the DNA (SEQ ID NO:3) and translated sequence (SEQ ID NO:4) of RON6 VL region, with CDRs shown in singleunderline.

FIG. 1C illustrates the DNA (SEQ ID NO:5) and translated sequence (SEQ ID NO:6) of RON8 VH region, with CDRs shown in singleunderline.

FIG. 1D illustrates the DNA (SEQ ID NO:7) and translated sequence (SEQ ID NO:8) of RON8 VL region, with CDRs shown in singleunderline.

FIGS. 2A, 2B and 2C, together illustrate the complete RON6-H (Human IgG1 subgroup I) DNA (SEQ ID NO:9) and amino acid sequence (SEQ ID NO:10). Secretory signal sequence (italic); variable region (doubleunderline, except for the CDR domains); CDR domains (singleunderline); gamma constant region (unmodified). The asterisk (*) indicates the STOP codon.

FIGS. 2D-2E together illustrate the complete RON6-L (human kappa light chain subgroup III), DNA (SEQ ID NO:11) and amino acid sequence (SEQ ID NO:12). RON6-L secretory signal sequence (italic); variable region (doubleunderline, except for the CDR domains); CDRs (singleUnderline); kappa constant region (unmodified).

FIGS. 3A-3C together illustrate the complete RON8-H DNA (SEQ ID NO:13) and amino acid (SEQ ID NO:14) sequence. Secretory signal sequence (italic), variable region (double underline) with CDRs (underline), gamma constant region (unmodified) The asterisk (*) indicates the STOP codon. The complete RON8-H amino acid sequence without secretory signal sequence is SEQ ID NO:50.

FIGS. 3D-3E illustrates the complete RON8-L DNA (SEQ ID NO:15) and amino acid (SEQ ID NO:16) sequence. Secretory signal sequence (italic), variable region (double underline, except for the CDR domains) with CDRs (underline), kappa constant region (unmodified). The asterisk (*) indicates the STOP codon. The complete RON8-L amino acid sequence without secretory signal sequence is SEQ ID NO:51.

The RON6 and RON8 antibodies, respectively, are confirmed to inhibit MSP-dependent activation of the RON receptor and activation of signal transduction pathways downstream to the RON receptor. For FIG. 5A, NIH3T3-RON cells were starved overnight, treated for 2 hours with the indicated antibody concentration and than stimulated with 10 nM MSP for 10 min. Following stimulation, cells were lysed and total cell lysates were separated by SDS-PAGE and probed with the indicated antibodies. For FIG. 5B, H-292 cells were starved overnight, treated for 2 hours with the indicated antibody concentration and then stimulated with 10 nM MSP for 10 min. Following stimulation, cells were lysed and total cell lysates were separated by SDS-PAGE and probed with the indicated antibodies. For FIG. 5C, HT-29 cells were starved overnight, treated for 2 hours with the indicated antibody concentration and than stimulated with 10 nM MSP for 10 min. Following stimulation, cells were lysed and total cell lysates were separated by SDS-PAGE and probed with the indicated antibodies.

Figure 6A:
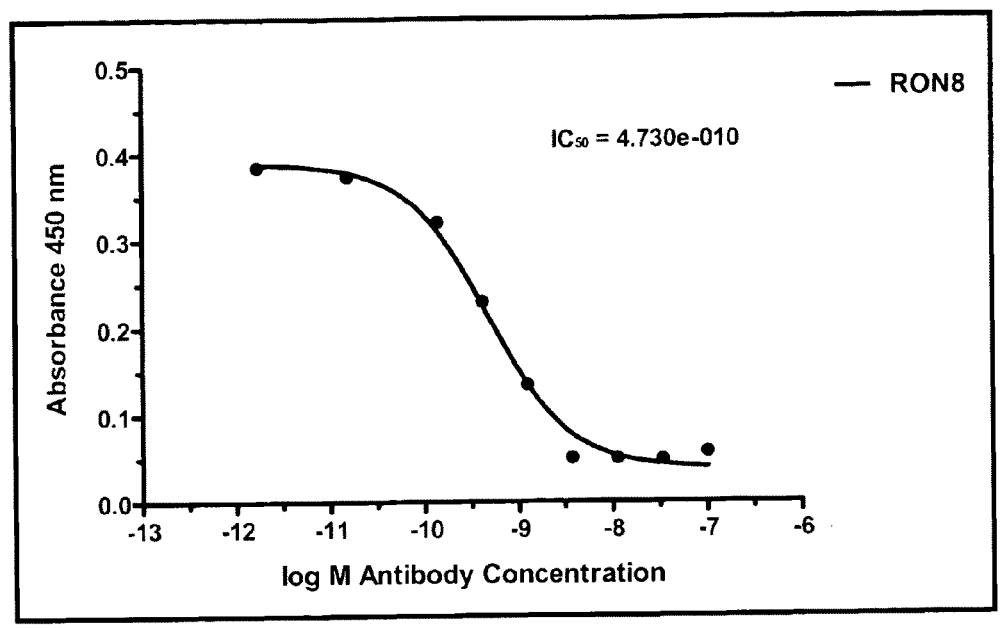

FIG. 6A illustrates the solid-phase blocking characteristic of RON8 antibody. ELISA was used to determine the IC50 value of RON8 antibody needed to block the interaction of recombinant human RON protein to immobilized recombinant human MSP.

Figure 6B:
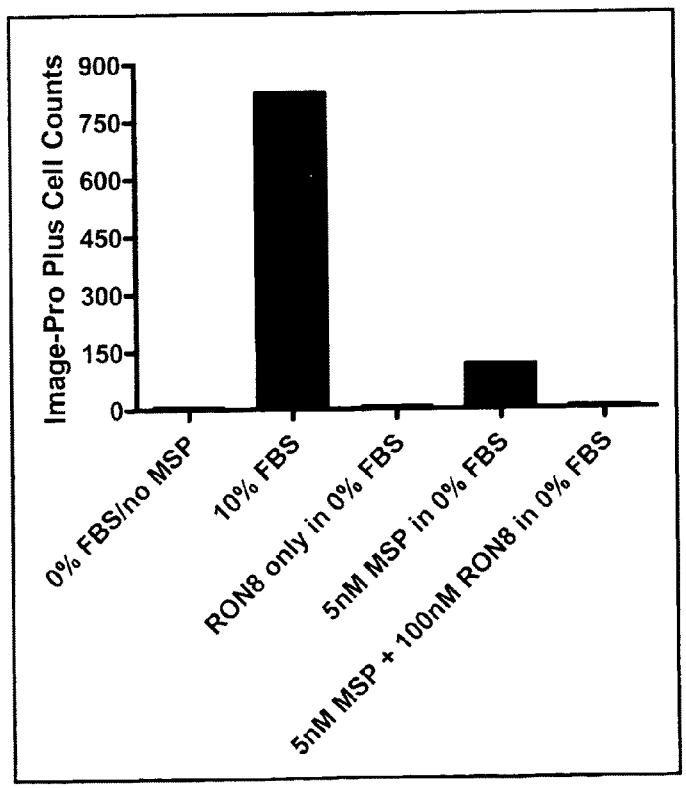

FIG. 6B illustrates the ability of RON8 antibody to inhibit cell migration of H596 lung cancer cells.

FIG. 6C illustrate RON8 antibody inhibition of MSP-induced DNA synthesis in BXPC3 pancreatic cancer cells.

FIG. 6C(1) illustrates MSP stimulation of [3H]-Thymidine incorporation, a measure of DNA synthesis.

FIG. 6C(2) illustrates a system in which cells were pre-treated with RON8 antibody for 1 hour prior to the addition of MSP.

DETAILED DESCRIPTION OF THE INVENTION

The present invention provides anti-RON antibodies having utility, e.g., in assays for detecting RON proteins for diagnostic purposes, and in methods of inhibiting RON activity for therapeutic purposes. Further, the inventive anti-RON antibodies may be administered to an animal, e.g., a mammal such as a human, in a therapeutically effective amount, e.g., an amount effective to inhibit growth, proliferation, metastatic activity (i.e. migration and/or invasion) of any and all tumor cells that express RON. The invention also provides pharmaceutical compositions comprising the disclosed anti-RON antibodies, or fragments thereof. Further, the present invention provides fully human antibodies that bind to the human RON receptor tyrosine kinase. Such antibodies include but are not limited to the exemplified RON6 and RON8 and active or functional fragments and derivatives thereof.

For clarity of description, it should be appreciated that the target protein is called RON, as detailed by the above provided Background section, and the preferred anti-RON antibodies exemplified herein are designated as "RON6" and "RON8" respectively. Using a screening process, the anti-RON antibodies of the present invention were selected from among hundreds of candidate anti-RON antibodies. The antibodies of the present invention exhibit unexpectedly desirable RON-binding characteristics, relative to previously available anti-RON antibodies, as described in detail in the examples below. In particular, the new RON6 and RON8 antibodies have an affinity for the RON receptor that is 100 fold greater than RON1, a fully human anti-RON antibody previously generated from a phage library system. Specifically, RON6 and RON8 bind RON with a $K_D$ of $4.1 \times 10^{-11}$ and $3.2 \times 10^{-11}$ M, respectively whereas RON1 binds RON with a $K_D$ of $7.7 \times 10^{-9}$ M. RON1 is the current designation of art-known antibody, described in International Patent Appl. No. WO2005120557, Id., incorporated by reference herein.

As referred to herein, CDR sequence information disclosed herein for use with the methods of the present invention may be "derived", i.e., based on, created, or having originated from, sequence information from any and all possible sources of antibody variable domains, which can include wild type or variant forms, as well as naturally occurring or synthetically produced, according to methods familiar to one of skill in the art.

Reference herein to "tumor" is intended to include cancer generally, and both malignant and nonmalignant disease, unless otherwise specified. As contemplated herein, malignant tumors include primary and secondary tumors. Primary tumors arise directly from the tissue in which they are found. A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that may be included for possible treatment using the methods of the present invention include, but are not limited to, leukemias, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, non-small cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, lymphomas, malignant melanomas, epidermoid carcinomas, and other carcinomas and sarcomas.

For clarity, it is also intended that the use of singular terms for convenience in the description is in no way intended to be so limiting. Thus, for example, reference to "an antibody" or "a tumor" includes reference to one or more of such antibodies or tumors. The use of plural terms is also not intended to be limiting, unless otherwise specified.

The antibodies of the present invention, or fragments thereof, specific for RON, neutralize activation of the RON receptor. As used herein, neutralizing a receptor means inactivating the intrinsic kinase activity of the receptor to transduce a signal. A reliable assay for RON neutralization is the inhibition of receptor phosphorylation.

The present invention is not limited by any particular mechanism of RON neutralization. Such neutralization, for example, may occur by an antibody blocking access of certain epitopes to a ligand, or by changing the conformation of RON in certain manner that the ligand, particularly MSP, cannot activate the receptor even though it can bind to the receptor. U.S. Pat. No. 6,165,464 lists various possible mechanisms for such neutralization, including antibodies binding to the ligand itself, the antibodies down regulating the receptor, the antibodies inhibiting the tyrosine kinase activity of the receptor or the antibodies eliciting a cytotoxic response. Down-regulation may occur when cells which express RON, particularly those that over express (including differentially express) RON, decrease the number of RON receptor tyrosine kinases on their surface. Hence, neutralizing has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

Neutralization of RON by an anti-RON antibody may also include neutralization of a variant RON receptor tyrosine kinase that is active without ligand binding or binds to ligand and does not consequently deactivate. Thus RON neutralization may include neutralization of wild type and/or variant RON (point mutations, deletions, alternative splicing, etc.).

As used herein, the term, "variant" of RON optionally includes RON proteins that are shorter or longer than the wild-type RON, and optionally will include analogs containing amino acid substitutions. Variants of RON can also result from alternative mRNA splicing or initiation and/or point mutation(s).

One useful measure of the degree of RON neutralization by an anti-RON antibody is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., J. Pharmacol. Exp. Thera. 283: 1433-44 (1997) and Batley et al., Life Sci. 62:143-50 (1998).

Another measure of RON neutralization is inhibition of phosphorylation of downstream substrates of RON. Accordingly, the level of phosphorylation of MAPK or Akt, for example, can be measured.

Naturally occurring antibodies typically have two identical heavy chains and two identical light chains, with each light chain covalently linked to a heavy chain by an inter-chain disulfide bond and multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains (CHI, CH2, CH3 and CH4). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hypervariable or complementarity-determining regions (CDRs), are found in each of VL and VH, which are supported by less variable regions called framework variable regions.

The inventive antibodies as exemplified include IgG monoclonal antibodies. It is also contemplated that an "antibody" or "antibodies" according to the invention may comprise antibody fragments or engineered forms. These are, for example, Fv fragments, or proteins wherein the CDRs and/or variable domains of the exemplified antibodies are engineered as single-chain antigen-binding proteins, diabodies and/or triabodies, in order to provide the advantages of the new inventive antibodies in alternative structural forms.

In brief, the portion of an antibody consisting of the VL and VH domains is designated as an Fv (Fragment variable) and constitutes the antigen-binding site. A single chain Fv (scFv or SCA) is an antibody fragment containing a VL domain and a VH domain on one polypeptide chain, wherein the N terminus of one domain and the C terminus of the other domain are joined by a flexible linker (see, e.g., U.S. Pat. No. 4,946,778 (Ladner et al.); WO 88/09344, (Huston et al.). WO 92/01047 (McCafferty et al.) describes the display of scFv fragments on the surface of soluble recombinant genetic display packages, such as bacteriophage.

The peptide linkers used to produce the single chain antibodies can be flexible peptides selected to assure that the proper three-dimensional folding of the VL and VH domains occurs. The linker is generally 10 to 50 amino acid residues. Preferably, the linker is 10 to 30 amino acid residues. More preferably the linker is 12 to 30 amino acid residues. Most preferably is a linker of 15 to 25 amino acid residues. An example of such linker peptides includes repeats of four glycines followed by serine.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one VH and one VL domain covalently linked by a first peptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Simply by way of example, a diabody according to the invention may be bispecific and comprise both a RON6 AND RON8 binding domain.

Three single chain antibodies can be combined to form triabodies, also known as trivalent dimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Fab (Fragment, antigen binding) refers to the fragments of the antibody consisting of VL CL VH CH1 domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. F(ab')2 fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement-mediated cytotoxicity and antibody-dependent cellular-cytotoxicity (ADCC). For antibodies such as IgA and IgM, which are complexes of multiple IgG like proteins, complex formation requires Fc constant domains.

Finally, the hinge region separates the Fab and Fc portions of the antibody, providing for mobility of Fabs relative to each other and relative to Fc, as well as including multiple disulfide bonds for covalent linkage of the two heavy chains.

Thus, antibodies specific to RON include, but are not limited to, naturally occurring antibodies and fragments thereof. Such fragments include, simply by way of example, bivalent fragments such as (FaV)2, monovalent fragments such as Fab, single chain antibodies, single chain Fv (scFv), single domain antibodies that bind specifically to RON. Preferably such fragments include one or more of the CDRs of the RON6 and/or RON8 antibodies exemplified herein. The definition of antibodies according the invention optionally further includes engineered antibodies that bind specifically to RON, such as multivalent single chain antibodies, diabodies, triabodies, and the like that bind specifically with antigens. Preferably such multivalent engineered antibodies include one or more of the CDRs of the RON6 and/or RON8 antibodies exemplified herein.

Each domain of the antibodies of this invention can be a complete antibody with the heavy or light chain variable domain, or it can be functionally the same or a mutant or derivative of a naturally-occurring domain, or a synthetic domain constructed, for example, in vitro using a technique such as one described in WO 93/11236 (Griffiths et al.). For instance, it is possible to join together domains corresponding to antibody variable domains, which are missing at least one amino acid. The important characterizing feature is the ability of each domain to associate with a complementary domain to form an antigen-binding site. Accordingly, the terms variable heavy and light chain fragment should not be construed to exclude variants that do not have a material effect on specificity.

As used herein, the terms "antibodies" and "antibody fragments" include modifications that retain specificity for the RON receptor. Such modifications include, but are not limited to, conjugation to an effector molecule such as a chemotherapeutic agent (e.g., cisplatin, taxol, doxorubicin) or cytotoxin (e.g., a protein, or a non-protein organic chemotherapeutic agent). The antibodies can be modified by conjugation to detectable reporter moieties. Also included are antibodies with alterations that affect non-binding characteristics such as half-life (e.g., conjugation to polyetheylen glycol polymers).

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990) for the conjugation of doxorubicin and those described by Amon et al., Adv. Exp. Med. Biol. 303, 79-90 (1991) and by Kiseleva et al., Mol. Biol. (USSR) 25, 508-514 (1991) for the conjugation of platinum compounds.

Antibody "specificity" refers to selective recognition of the antibody for a particular epitope of an antigen. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational". In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen.

Epitope Mapping and Related Technologies

To screen for antibodies which bind to a particular epitope (e.g., those which block binding of IgE to its high affinity receptor), a routine cross-blocking assay such as that described in Harlow and Lane, ANTIBODIES (1990) Cold Spring Harbor Laboratory Press, can be performed. Other methods include alanine scanning mutants, peptide blots (Reineke, 2004 Methods Mol Biol 248:443-63) (herein incorporated by reference in its entirety), or peptide cleavage analysis. In addition, methods such as epitope excision, epitope extraction and chemical modification of antigens can be employed (Tomer, 2000 Protein Science: 9: 487-496, herein specifically incorporated by reference in its entirety).

Functional Analysis

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US Patent Publication No. 2004/0101920, incorporated by reference herein in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the RON6 and RON8 antibodies of the present invention into groups of antibodies capable of binding different epitopes.

Antibodies or fragments thereof, of the present invention can be monospecific or bispecific. Bispecific antibodies (BsAbs) are antibodies that have two different antigen-binding specificities or sites (See U.S. Publication No. 2004/0259156, filed Feb. 13, 2004). Where an antibody has more than one specificity, the recognized epitopes can be associated with a single antigen or with more than one antigen. Thus, the present invention provides bispecific antibodies, or fragments thereof, that bind to two different antigens, with at least one specificity for RON.

Specificity of antibodies, or fragments thereof, for RON can be determined based on affinity and/or avidity. Affinity, represented by the equilibrium constant for the dissociation of an antigen with an antibody ("Kd"), measures the binding strength between an antigenic determinant and an antibody-binding site. Avidity is the measure of the strength of binding between an antibody and its antigen. Avidity is related to both the affinity between an epitope with its antigen binding site on the antibody, and the valence of the antibody, which refers to the number of antigen binding sites of a particular epitope. Antibodies typically bind with a dissociation constant (Kd) of about $10^{-5}$ to about $10^{-11}$ liters/mol (e.g., KD<100 nM). Any Kd less than about 10-4 liters/mol is generally considered to indicate nonspecific binding. The lesser the value of the Kd, the stronger the binding strength between an antigenic determinant and the antibody binding site.

RON may be isolated from various sources to raise an immune response, such as from cells that express RON: colon, pancreatic, prostate, stomach, lung, liver, ovarian, kidney, breast and brain, and in general epithelial and neuroendocrine cells. Also, a synthetic receptor peptide may be obtained using commercially available machines and the corresponding amino acid sequence. A further alternative still, is that DNA encoding a RON protein such as a cDNA or a fragment thereof, may be cloned and expressed and the resulting polypeptide recovered and used as an immunogen to raise an antibody of the invention. In order to prepare a RON protein or fragment thereof against which the antibodies are made, nucleic acid molecules that encode RON, or portions thereof, especially the extracellular portions thereof (particularly alpha and beta portion), may be inserted into known vectors for expression in host cells using standard recombinant DNA techniques. Similarly, antibodies against ligands of RON, particularly MSP, may be prepared.

The sequences for RON and its ligand MSP are publicly available in the GenBank database (RON accession number X70040 and MSP accession number NM 020998, both citations are incorporated by reference herein), and can readily be used for antibody preparation. Antibodies may also be produced against variants/mutants of RON or MSP. Of interest are antibodies to epitopes present on extracellular domains of variants and mutants. An altered RON receptor differing by an in-frame deletion of 109 amino acids in the extracellular domain has been shown to be constitutively activated (1). Antibodies may for example be generated against such altered RON receptor.

Antibodies specific to RON may be prepared by immunizing a mammal with RON. The soluble receptors may be used by themselves as immunogens, or attached to a carrier protein or other objects, such as beads, i.e. sepharose beads. After the mammal has produced antibodies, a mixture of antibody producing cells, such as splenocytes, are isolated. Monoclonal antibodies may be produced by isolating individual antibody-producing cells from the mixture and immortalizing them by, for example, fusing them with tumor cells, such as myeloma cells. The resulting hybridomas are preserved in culture, and express monoclonal antibodies, which are harvested from the culture medium.

Further, antibodies and antibody fragments of the invention can be obtained by standard hybridoma technology (Harlow & Lane, ed., ANTIBODIES: A Laboratory Manual, Cold Spring Harbor, 211-213 (1998), which is incorporated by reference herein) using transgenic mice that produce human immunoglobulin heavy and light chains. In a preferred embodiment, a substantial portion of the human antibody producing genome is inserted into the genome of the mouse, and is rendered deficient in the production of endogenous murine antibodies. Such mice may be immunized subcutaneously (s.c.) with RON in complete Freund's adjuvant. The antibodies of this invention can be fused to additional amino acid residues. Such amino acid residues can be a peptide tag, perhaps to facilitate isolation. Other amino acid residues for homing of the antibodies to specific organs or tissues are also contemplated.

Anti-RON antibodies according to the present invention can be isolated from a phage display library such as one constructed from human heavy chain and light chain variable region genes. For example, a variable domain of the invention can be obtained from peripheral blood lymphocytes which contain a rearranged variable region gene. Alternatively, variable domain portions, such as CDR and FW regions, can be obtained from different human sequences.

The antibodies specific to RON bind to RON with a Kd of preferably about $1\times10^{-9}$ M-1 or less, more preferably about $1\times10^{-10}$ M$^{-1}$ or less, and most preferably about $1\times10^{-11}$M$^{-1}$ or less.

Antibodies or fragments thereof specific for RON inhibit activation of the receptor. Inhibiting a receptor means preventing the activation of the intrinsic kinase activity of the receptor to transduce a signal. A reliable assay for RON is the inhibition of receptor phosphorylation.

The present invention is not limited by any particular mechanism of RON inhibition. Such inhibition for example may occur by an antibody blocking access to certain epitopes by a ligand, or by changing conformation of RON in a manner that the ligand, particularly MSP, can not activate the receptor even though it can bind to the receptor. U.S. Pat. No. 6,165,464 lists various possible mechanisms for such inhibition, including binding to the ligand itself, down regulating the receptor, inhibiting the tyrosine kinase activity of the receptor, or eliciting a cytotoxic response. Down regulation may occur when cells which express RON, particularly those that over express (including differentially express) RON, decrease the number of RON receptor tyrosine kinases on their surface. Matrix metalloproteinases, which function in tumor cell invasion and metastasis, may also be down regulated by the antibodies of the present invention.

RON inhibition has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

The invention also contemplates antibodies that bind to and inactivate variant or mutated RON receptor tyrosine kinases that are active without ligand binding. A mammal suffering from a RON related disease may, for example, express both wild type and variant RON, with a disproportionate amount of the variant receptor expressed. Of interest are sequences of variants/mutants differing in the extracellular domain, such as those having deletions within the extracellular domain, as disclosed by Wang (1) (9). Thus RON inhibition may involve wild type and/or variant RON (point mutations, deletions, alternative splicing, etc.).

RON activation may occur through dimerization and activation with other RTKs such as c-met or EGFR. Thus, RON inhibition may also include inhibition of heterodimerization between RON and other receptor tyrosine kinases (RTKs) such as EGFR or c-met. Such inhibition may also include inhibition of signaling by a formed heterodimer of RON and EGF or c-met as an example. Such dimerization may have been induced in a ligand dependent fashion, such as by MSP, HGF or EGF binding to their receptors and inducing dimerization.

One measure of RON inhibition is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining inhibiting antibodies in the context of the present invention. Phosphorylation can be detected, for example, using an antibody specific for phosphotyrosine in an ELISA assay or on a Western blot. Some assays for tyrosine kinase activity are described in Panek et al., J. Pharmacol. Exp. Them. 283: 1433-44 (1997) and Batley et al., Life Sd. 62:143-50 (1998) [52]. In addition, methods for detection of protein expression can be utilized to determine RON inhibition. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA.

Another measure of RON inhibition includes the level of phosphorylation of downstream substrates of RON. Accordingly, the level of phosphorylation of MAPK or Akt, for example, can be measured.

In one embodiment, an antibody specific to RON having one, two, three, four, five, or all six complementarity-determining regions (CDRs) of the antibodies of the present invention is administered to a mammal. In another embodiment, the antibody administered has the variable regions of the antibodies of the present invention. FIGS. 2A-2E provide the sequences of antibodies of the present invention. Without intending to be bound by theory, It is believed that RON6 and RON8 bind to the beta extracellular domain of RON, but such specificity may also arise by binding to other domains of RON, or by binding to different epitopes in the same domain. CDRs of the RON6 and RON8 antibodies isolated according to the present invention include:

```
          RON6 VH
CDR1   G   G   T   F   S   S   D   A   I   T           (SEQ ID NO:17)
       GGA GGC ACC TTC AGC AGC GAT GCT ATC ACC         (SEQ ID NO:18)

CDR2   G   I   I   P   I   L   G   M   A   N   Y   A   (SEQ ID NO:19)
       GGG ATC ATC CCT ATC CTT GGT ATG GCA AAC TAC GCA (SEQ ID NO:20)

Q   K   F   Q   G
       CAG AAG TTC CAG GGC

CDR3   V   A   D   Y   Y   G   L   G   T               (SEQ ID NO:21)
       GTG GCC GAT TAC TAT GGT TTG GGG ACT             (SEQ ID NO:22)

Y   Y   W   Y   F   D   L
       TAC TAC TGG TAC TTC GAT CTC

RON6 VL
CDR1   R   A   S   Q   S   V   S                       (SEQ ID NO:23)
       AGG GCC AGT CAG AGT GTT AGC                     (SEQ ID NO:24)

CDR2   G   A   S   S   W   A   T                       (SEQ ID NO:25)
       GGT GCA TCC AGC TGG GCC ACT                     (SEQ ID NO:26)

CDR3   Q   Q   Y   G   S   S   P   L   T               (SEQ ID NO:27)
       CAG CAA TAT GGT AGC TCA CCT CTC ACT             (SEQ ID NO:28)

RON8 VH
CDR1   G   F   T   F   S   S   Y   L   M   T           (SEQ ID NO:29)
       GGA TTC ACC TTT AGT AGT TAT TTA ATG ACC         (SEQ ID NO:30)

CDR2   N   I   K   Q   D   G   S   E   K   Y           (SEQ ID NO:31)
       AAC ATA AAG CAA GAT GGA AGT GAG AAA TAC         (SEQ ID NO:32)
```

-continued

```
         Y   V   D   S   V   K   G
        TAT GTG GAC TCT GTG AAG GGC

CDR3     D   G   Y   S   S   G   R                    (SEQ ID NO:33)
        GAT GGC TAT AGT TCG GGG AGA                   (SEQ ID NO:34)

H   Y   G   M   D   V
        CAC TAC GGT ATG GAC GTC

RON8 VL
CDR1     R   A   S   Q   S   V   S                    (SEQ ID NO:35)
        AGG GCC AGT CAG AGT GTT AGC                   (SEQ ID NO:36)

R   Y   L   A
        AGA TAC TTA GCC

CDR2     D   A   S   N   R   A   T                    (SEQ ID NO:37)
        GAT GCA TCC AAC AGG GCC ACT                   (SEQ ID NO:38)

CDR3     Q   Q   R   S   N   W   P   R   T            (SEQ ID NO:39)
        CAG CAG CGT AGC AAC TGG CCT CGG ACG           (SEQ ID NO:40)
```

Functional variants of antibodies and antibody fragments specific to RON also include polypeptides with amino acid sequences substantially similar to the amino acid sequence of the variable or hypervariable regions of the antibodies of the present invention. Substantially the same amino acid sequence is defined herein as a sequence with at least 70%, preferably at least about 80%, and more preferably at least about 90% homology to a compared amino acid sequence, as determined by the FASTA search method in accordance with Pearson and Lipman, Proc. Natl. Acad. Sci. USA 85, 2444-2448 (1988), including sequences that are at least about 70%, preferably at least about 80%, and more preferably at least about 90%, 95% or 99% identical and all subranges therebetween. Such antibodies will have the same or similar binding, ligand blocking, and receptor inhibiting activities to antibodies of the invention that have substantially the same CDRs.

Variants of antibodies and antibody fragments specific to RON also include antibodies having one or more conservative amino acid substitutions. A conservative amino acid substitution is defined as a change in the amino acid composition by way of changing one, two or more amino acids of a peptide, polypeptide or protein, or fragment thereof. The substitution is of amino acids with generally similar properties (e.g., acidic, basic, aromatic, size, positively or negatively charged, polarity, non-polarity) such that the substitutions do not substantially alter peptide, polypeptide or protein characteristics (e.g., charge, isoelectric point, affinity, avidity, conformation, solubility) or activity. Typical substitutions that may be performed for such conservative amino acid substitution may be among the groups of amino acids as follows: glycine (G), alanine (A), valine (V), leucine (L) and isoleucine (I); aspartic acid (D) and glutamic acid (E); alanine (A), serine (S) and threonine (T); histidine (H), lysine (K) and arginine (R): asparagine (N) and glutamine (Q); phenylalanine (F), tyrosine (Y) and tryptophan (W).

Conservative amino acid substitutions can be made in, e.g., regions flanking the hypervariable regions primarily responsible for the selective and/or specific binding characteristics of the molecule, as well as other parts of the molecule, e.g., variable heavy chain cassette.

Antibodies, or fragments thereof, also include those for which binding characteristics have been improved by direct mutation, methods of affinity maturation, phage display, or chain shuffling.

Affinity and specificity can be modified or improved by mutating CDR and/or FW residues and screening for antigen binding sites having the desired characteristics (see, e.g., Yang et al, J. Mol. Biol., (1995) 254: 392-403). One way is to randomize individual residues or combinations of residues so that in a population of otherwise identical antigen binding sites, subsets of from two to twenty amino acids are found at particular positions. Alternatively, mutations can be induced over a range of residues by error prone PCR methods (see, e.g., Hawkins et al., J. Mol. Biol, (1992) 226: 889-96). In another example, phage display vectors containing heavy and light chain variable region genes can be propagated in mutator strains of *E. coli* (see, e.g., Low et al., J. Mol. Biol., (1996) 250: 359-68). These methods of mutagenesis are illustrative of the many methods known to one of skill in the art.

Another manner for increasing affinity of the antibodies of the present invention is to carry out chain shuffling, where the heavy or light chain are randomly paired with other heavy or light chains to prepare an antibody with higher affinity. The various CDRs of the antibodies may also be shuffled with the corresponding CDRs in other antibodies.

Additionally, the present invention provides isolated polynucleotides encoding the present antibodies or fragments thereof as well as expression vectors comprising these polynucleotide sequences operably linked to an expression sequence. These nucleotides are listed in FIGS. 1A-1D, 2A-2E, and 3A-3E. Recombinant host cells comprising one or more expression vectors which express the present antibodies, or fragments thereof, are also provided. Methods are also provided for producing antibodies or fragments thereof comprising culturing these cells under conditions permitting expression of the antibodies or fragments thereof. The antibodies or fragments thereof can then be purified from the cell or cell culture medium.

Variants of the nucleotides listed in FIGS. 1A-1D, 2A-2E, and 3A-3E include those that encode for an antibody, or antibody fragment, having the same function as the antibodies of the present invention, i.e., to block or inhibit activation of RON. Such variants have a sequence that is at least about 70%, preferably at least about 80%, and more preferably at least about 90% identical to wild-type RON. The present invention also provides for antibody fusion proteins. These fusion proteins may be encoded by the nucleotide sequences of FIGS. 1A-1D, 2A-2E, and 3A-3E that have been operatively connected to nucleotide sequences encoding enzymes, florescent proteins, a polypeptide tag or luminescent marker, and/or combinations thereof.

The nucleotide sequences of the invention also include: (a) the antibody DNA sequences shown in FIGS. 1A-1D, 2A-2E, and 3A-3E; (b) any nucleotide sequence that (i) hybridizes to a complement of the nucleotide sequence(s) set forth in (a) under stringent conditions, e.g., hybridization to filter-bound DNA in 0.5M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, CURRENT PROTOCOLS IN MOLECULAR BIOLOGY, Vol. I, Green Publishing Associates, Inc., and John Wiley & sons, Inc., New York, at p. 2.10.3) and (ii) encodes antibody or antibody fragment having substantially the same functionality; and (c) any nucleotide sequence that hybridizes to a DNA sequence that encodes the antibody sequences shown in FIGS. 2A-2E, and 3A-3E under less stringent conditions, such as moderately stringent conditions, e.g., washing in 0.2×SSC/0.1% SDS at 42° C. (Ausubel et al., 1989 supra), yet which still encodes an antibody or antibody fragment having substantially the same functionality. The functionality of the antibodies of the present invention is to block activation of RON.

The present invention also provides an expression vector containing a nucleic acid encoding an antibody of the present invention, or fragment thereof, operably linked to a control sequence, as well as a host cell containing such an expression vector. These host cells can be cultured under specific conditions permitting expression of antibodies of the present invention, or fragments thereof, and the antibodies then can be purified from the host cells.

Standard recombinant techniques and known expression vectors are used to express the antibodies of the invention. Vectors for expressing proteins in bacteria, especially *E. coli*, are known. Such vectors include the PATH vectors described by Dieckmann and Tzagoloff in J. Biol. Chem. 260, 1513-1520 (1985). These vectors contain DNA sequences that encode anthranilate synthetase (TrpE) followed by a polylinker at the carboxy terminus. Other expression vector systems are based on beta-galactosidase (pEX); lambda PL; maltose binding protein (pMAL); and glutathione S-transferase (pGST). See, Gene 67, 31 (1988) and Peptide Research 3, 167 (1990).

Vectors useful in yeast are available. A suitable example is the 2 D plasmid. Suitable vectors for expression in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Further eukaryotic expression vectors are known in the art (e.g., P. J. Southern and P. Berg, J. Mol. Appl. Genet. 1, 327-341 (1982); S. Subramani et al, Mol. Cell. Biol. 1, 854-864 (1981); R. J. Kaufmann and P. A. Sharp, "Amplification and Expression Of Sequences Cotransfected with A Modular Dihydrofolate Reductase Complementary DNA Gene," J. Mol. Biol. 159, 601-621 (1982); R. J. Kaufmann and P. A. Sharp, "Amplification and Expression Of Sequences Cotransfected with A Modular Dihydrofolate Reductase Complementary DNA Gene," J. Mol. Biol. 159, 601-664 (1982); S. I. Scahill et al, "Expression and Characterization Of the Product Of A Human Immune Interferon DNA Gene In Chinese Hamster Ovary Cells," Proc. Natl. Acad. Sci. USA 80, 4654-4659 (1983); G. Urlaub and L. A. Chasin, Proc. Natl. Acad. Sci. USA 77, 4216-4220, (1980)).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alphamating factors, and promoters derived from polyoma, adenovirus, retrovirus, and simian virus, e.g., the early and late promoters or SV40, and other sequences known to control the expression of genes of prokaryotic or eukaryotic cells and their viruses or combination thereof.

Vectors (recombinant and expression vectors) are contemplated for use as provided herein. For example, expression vectors containing the control signals and DNA to be expressed, such as those encoding antibodies of the invention or antibody fragments thereof, are inserted into a host cell for expression. Some useful expression host cells include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*. Suitable eukaryotic cells include yeast and other fungi, insect, animal cells, such as COS cells, cell lines of lymphoid origin such as lymphoma, myeloma (e.g. NSO) and CHO cells, human cells and plant cells in tissue culture.

A method of producing an antibody is provided. This method includes culturing the host cell that includes a suitable expression vector, wherein the expression vector comprises one or more nucleic acid molecules that encode a polypeptide, e.g., a heavy or light chain of such antibody, or fragments or engineered variants thereof, under conditions permitting expression of the polypeptide. Following expression in a host cell maintained in a suitable medium, the expressed polypeptide may be isolated from the medium, and purified by methods known in the art. If the polypeptide or peptide is not secreted into the culture medium, the host cells are lysed prior to isolation and purification. A purified antibody is one that has been identified and separated and/or recovered from a component of its natural environment. Contaminant components of its natural environment are materials, which would interfere with diagnostic or therapeutic uses for the antibody, and may include enzymes, hormones, and other proteinaceous or non-proteinaceous solutes, generally have been removed.

Thus, for example, monoclonal antibodies according to the invention are secreted by subclones that are be isolated or purified from the culture medium or ascites fluid by conventional immunoglobulin purification procedures such as, for example protein A-Sepharose, hydrolyapatite chromatography, gel electrophoresis, dialysis, or affinity chromatography.

In another embodiment, an inventive antibody that is specific to RON is produced by expressing one or more nucleic acids encoding light and/or heavy chains, or analogs thereof that comprise the antibody, in a transgenic animal, such that the antibody is expressed and can be recovered. For example, the antibody can be expressed in a tissue specific manner that facilitates recovery and purification. In one such embodiment, an antibody of the invention is expressed in the mammary gland for secretion during lactation. Transgenic animals include but are not limited to mice, goat, and rabbit. Any other art-known transgenic system may also be employed, e.g., expression in the albumen of avian eggs, e.g., chicken eggs.

The present invention provides for pharmaceutical compositions comprising the inventive anti-RON antibodies. In one embodiment, the composition may comprise one or more of the RON6 and/or RON8 anti-RON antibodies exemplified herein. It is understood that the anti-RON antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

"Carrier" as used herein includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

The active ingredients may also be entrapped in microcapsules prepared, for example, by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nanoparticles, and nanocapsules) or in macroemulsions. The formulations to be used for in vivo administration must be sterile. This is readily accomplished by filtration through sterile filtration membranes.

Sustained-release preparations may also be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular.

S—S bond formation through thio-disulfide interchange, stabilization may be achieved by modifying sulfhydryl residues, lyophilizing from acidic solutions, controlling moisture content, using appropriate additives, and developing specific polymer matrix compositions.

The present invention provides methods of treatment involving administration to a mammal in need thereof a therapeutically effective amount of antibodies or fragments thereof specific to RON as a monotherapy or in combination with other treatment options. In one embodiment the mammal is a human. Such antibodies may include chimeric, humanized, murine, rabbit and human antibodies, obtained by various techniques. In another embodiment the antibody administered is a human antibody. In another embodiment, said antibody comprises at least a single CDR sequence of RON6 or RON8. Conditions for which these methods are useful include tumors that express RON, inflammatory diseases, hyperproliferative diseases, and diseases of the liver, biliary tract, bile ducts, gall bladder and related hepatobiliary system.

As discussed herein, it is contemplated that the anti-RON antibodies of the present invention may be used to treat any pathological condition, including but not limited to, neoplastic or non-neoplastic conditions, as a monotherapy and/or in combination with other therapeutic agents. It is further contemplated that with regard to treatment of certain conditions, e.g., cancer, the antibodies may be used alone or in conjunction with other treatment agents as a front-line treatment strategy (e.g., as a first course of treatment in a newly diagnosed cancer patient) or as a second-line treatment strategy (e.g., treatment of a cancer patient who has been previously treated using other agents but has not responded to the first agent or has developed a resistance thereto).

Treatment means any treatment of a disease in a mammal and includes: (1) preventing the disease from occurring in a mammal which may be predisposed to the disease but does not yet experience or display symptoms of the disease; e.g., prevention of the outbreak of the clinical symptoms; (2) inhibiting the disease, e.g., arresting its development; or (3) relieving the disease, e.g., causing regression of the symptoms of the disease.

In the methods of the present invention, a therapeutically effective amount of an antibody of the invention is administered to a mammal in need thereof. The term "administering" as used herein means delivering the antibodies of the present invention to a mammal by any method that can achieve the result sought. They can be administered, for example, intravenously or intramuscularly. Although human antibodies of the invention are particularly useful for administration to humans, they can be administered to other mammals as well. The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect, such as inhibiting kinase activity or inhibition of tumor growth.

The present anti-RON antibodies can be administered for therapeutic treatments to a patient suffering from a tumor or angiogenesis associated pathologic condition in an amount sufficient to prevent, inhibit, or reduce the progression of the tumor or pathologic condition. Progression includes, e.g., the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

A suitable dose for the antibodies of the present invention may be determined based on the in vivo data illustrated in the present invention. The in vivo experiment used a dose of about 1 mg/20 grams every three days. The average mouse is about 0.02 Kg and its volume is about 0.008 m$^2$. The average human is about 70 Kg, and its volume is about 1.85 m$^2$. A dose of about 200 mg/m$^2$ corresponds to about 40 mg/Kg into a mouse, which is roughly about 2.6 mg/Kg in a human. To put this dose in perspective, another antibody, Erbitux®, is administered at 1 dose pre week of about 250 mg/m$^2$, which is about 6.5 mg/Kg in a human. Based on these calculations and experiments, the dose administered to a human is preferably about 1 to about 10 mg/Kg, more preferably about 3 to about 8 mg/Kg (1 dose per week). The dose might be similar to that for Erbitux®, e.g., about 6 to about 7 mg/Kg.

Figure 4A:
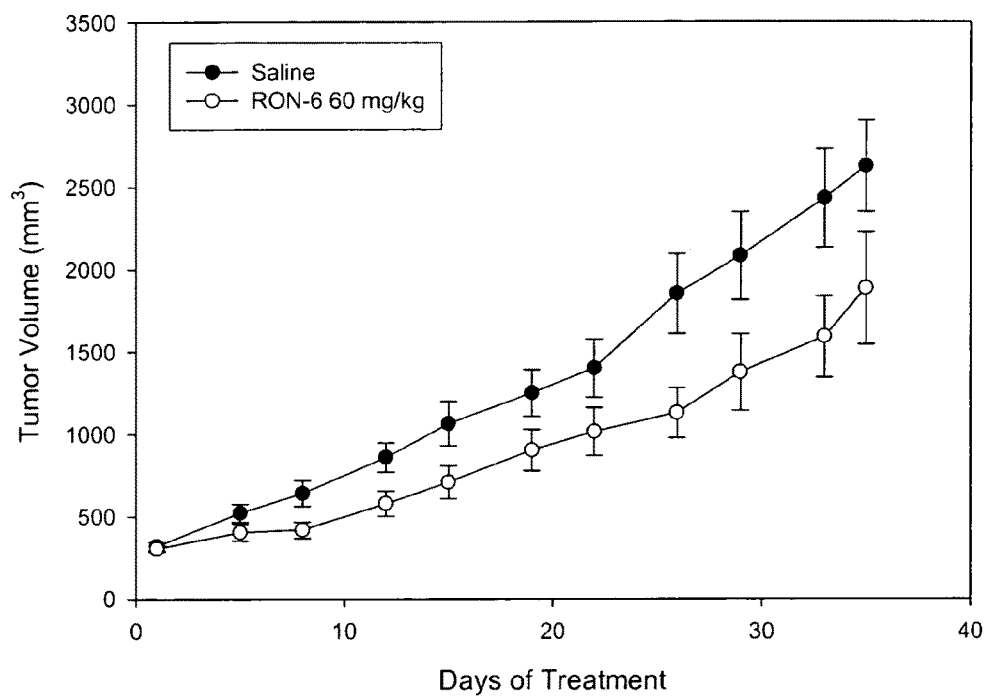
FIGS. 4C and 4D illustrate plots of tumor size verses time in the HT-29 mouse xenograft model. The charts show that the RON6 (FIG. 4C) and RON8 (FIG. 4C) antibodies inhibit growth of HT-29 tumor cells in the mouse xenograft system.
FIG. 4E illustrates plots of tumor size verses time in the BxPC3 mouse xenograft model with RON8 antibody alone, RON8 antibody plus Erbitux® (ERB), Erbitux® alone and Erbitux® in combination with a control IgG (hulgG antibodies). The chart shows that RON8 antibody (FIG. 4E) alone inhibits growth of BxPC3 tumor cells in the mouse xenograph system. The chart also shows that in combination with Erbitux®, there is a trend toward tumor regression or inhibition.
FIG. 4F illustrates that RON8 antibody inhibits the growth of breast tumor xenografts in nude mice. JIMT-1 breast cancer cells were injected subcutaneously into nude mice and allowed to grow to approximately 250 mm$^3$. Tumor volume is plotted during the course of treatment with Control (Saline), RON8 antibody (60 mg/kg, 2×/week), docetaxel, or the combination of docetaxel+RON8 antibody.
Figure 4B:
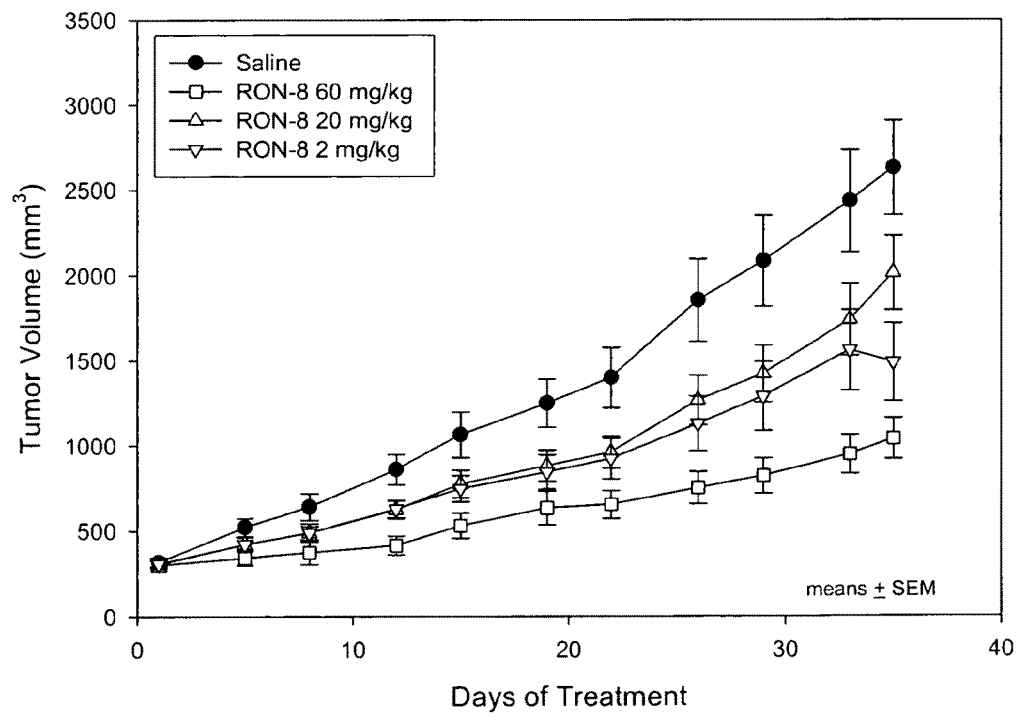
Figure 4C:
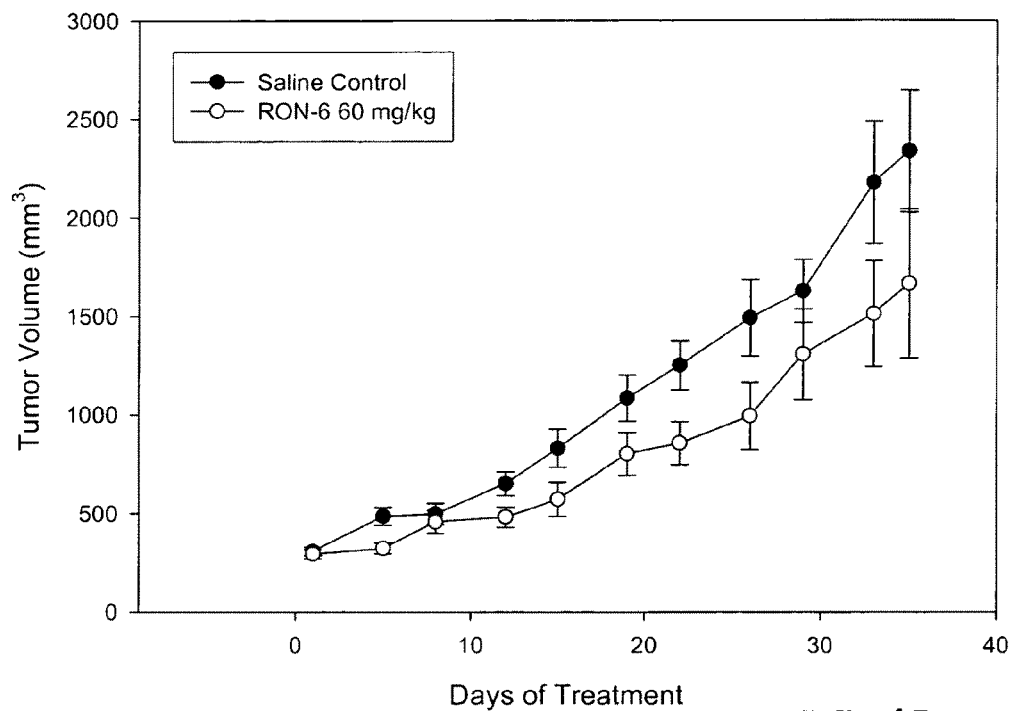
Figure 4D:
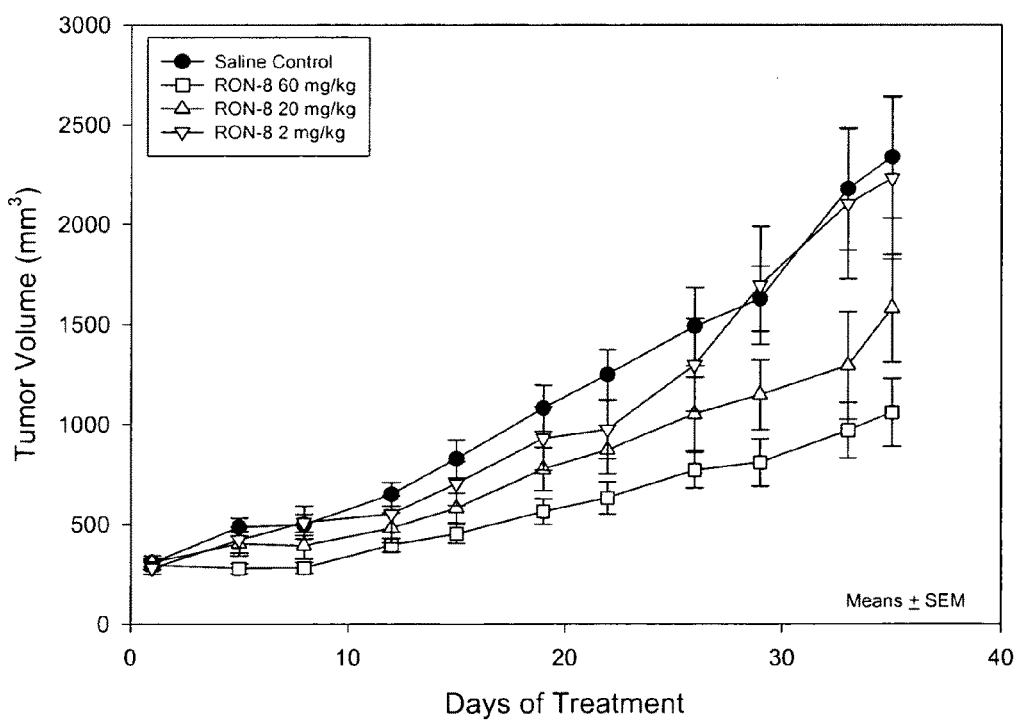

One embodiment of the invention contemplates that in vivo inhibition of RON with an antibody of the invention inhibits tumor growth. As shown in FIG. 4D, a RON antibody inhibits HT-29 cells grown subcutaneously in nude mice. In various embodiments, the tumor growth is suppressed at least about 20%, or at least about 40%. FIG. 4D shows about a 50-60% decrease in HT-29 tumor growth over a 40-day period.

Figure 5A:
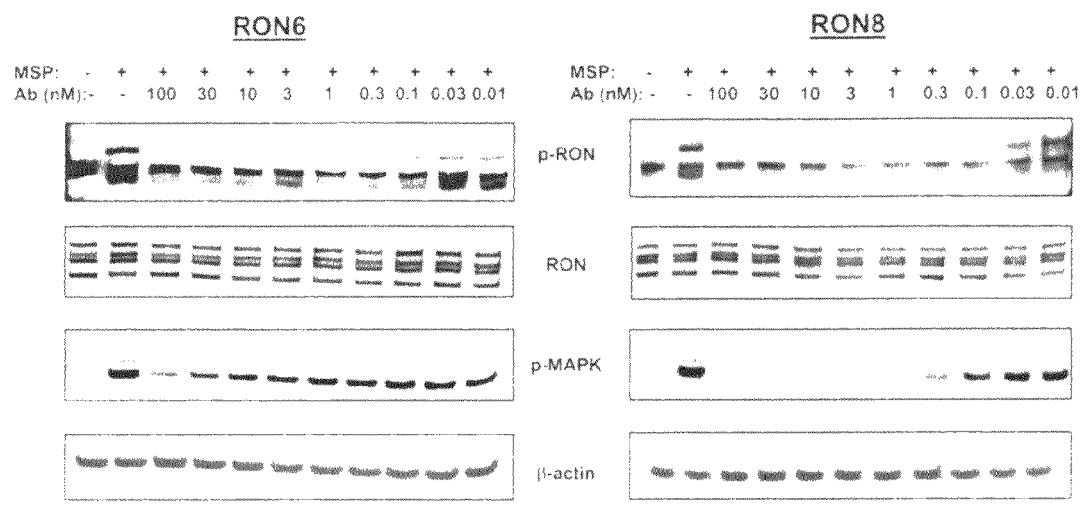
FIGS. 5A, 5B and 5C illustrate Western blots confirming inhibition of MSP induced phosphorylation by anti-RON antibodies RON6 and RON8.
Figure 5B:
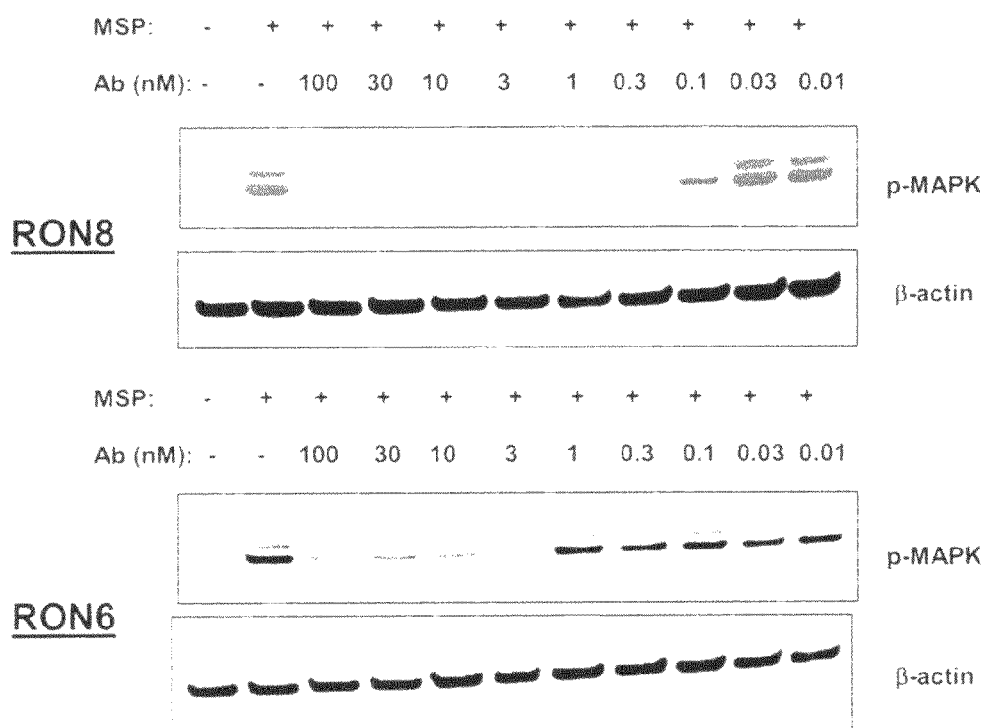
Figure 5C:
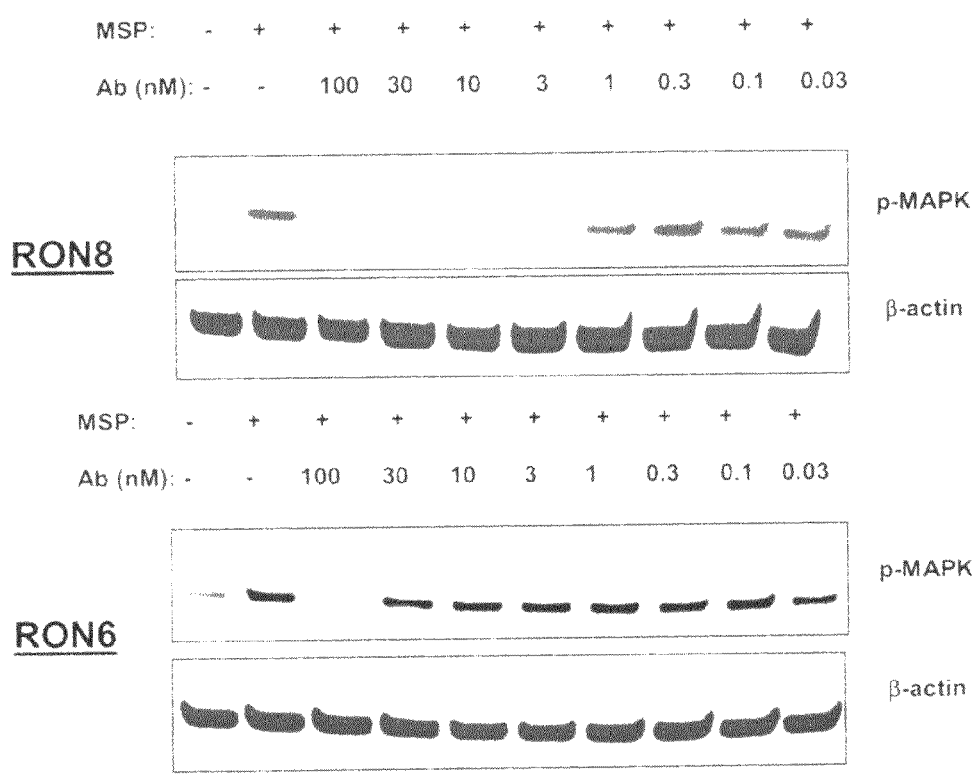

Anti-RON antibodies according to the invention can block, in various embodiments, at least about 60%, about 80%, or about 100%, of MSP-induced phosphorylation of RON, MAPK, and AKT (e.g., HT-29, Colo205, AGS and DU145). In FIG. 5A, the bands for lane 1 and 3 are almost identical, pointing to such complete blocking of phosphorylation. Phosphorylation of MAPK and AKT are considered important for cell proliferation (increase in cell number overtime), migration (movement of cells towards an agent, particularly MSP, i.e., chemo-attraction), invasion (ability to move through a new tissue) and survival. The proliferation of adherent HT-29 and Colo205 cells may be inhibited about 20% to about 30%, or about 25% in the presence of a RON antibody and 10% serum. In addition, when HT-29 and Colo205 are grown in soft agar in the presence of a RON antibody and 10% serum, colony formation may be inhibited about 60% to about 80%, more typically about 75% for HT-29, and about 50% to about 70%, more typically 60% for Colo205.

The invention is based on the observation that RON specific antibodies can inhibit growth of cancer cells in soft agar and inhibit proliferation while growing as adherent cells in cell culture conditions. A RON antibody can significantly retard the ability of the cancer cell line to form tumors when injected into nude mice, which demonstrates that inhibition of the RON receptor tyrosine kinase negatively influences the proliferation of colon cancer cells.

Using conventional Western blot and flow cytometry procedures, it has been found that RON is expressed in many human tumor cell lines: colon (HT-29, Colo205, HCT-116, DLD-I, Sw480, Sw620), pancreatic (BXPC-3, CAPAN-2, ASPC-I, HPAF-II, L3.7p1#7, Hs766T), prostate (DU-145, PC-3), stomach (AGS, NCI-N87), lung (A549, H596), liver (HepG2, SNU-182) and breast (JIMT1, DU4475, AU565). Accordingly, tumors derived from a variety of cell types are therapeutic targets for a RON antibody.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued.

Tumors that may be treated include tumors that are not vascularized, or not yet substantially vascularized, as well as vascularized tumors. Examples of solid tumors, which may be treated, include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas, and cerebral metastases, melanoma, gastrointestinal and renal carcinomas and sarcomas, rhabdomyosarcoma, glioblastoma, preferably glioblastoma multiforme, and leiomyosarcoma.

Of particular therapeutic interest are colon, pancreatic, prostate, stomach, lung and liver cancers, however, it is contemplated herein that any and all forms of pathological conditions, including neoplastic and non-neoplastic disease, in which administration of the antibodies of the present invention may result in a therapeutic benefit, are included within the scope of the present invention. Said pathological conditions may easily be determined by one of skill in the art and in light of the teachings provided herein.

Accordingly, the human anti-RON antibodies may be effective for treating subjects with vascularized tumors or neoplasms or angiogenic diseases. Such tumors and neoplasms include, for example, malignant tumors and neoplasms, such as blastomas, carcinomas or sarcomas, and highly vascular tumors and neoplasms. Cancers that may be treated by the methods of the present invention include, for example, cancers of the bladder, adrenal glands, testis, CNS and peripheral nervous system, brain, genitourinary tract, lymphatic system, stomach, renal system, colon, larynx, lung and bone. Non-limiting examples further include epidermoid tumors, squamous tumors, such as head and neck tumors, colorectal tumors, prostate tumors, breast tumors, lung tumors, including lung adenocarcinoma and small cell and non-small cell lung tumors, pancreatic tumors, thyroid tumors, ovarian tumors, and liver tumors. The method is also used for treatment of vascularized skin cancers, including squamous cell carcinoma, basal cell carcinoma, and skin cancers that can be treated by suppressing the growth of malignant keratinocytes, such as human malignant keratinocytes. Other cancers that may be treated include epithelial-mesenchymal transformation (EMT), Kaposi's sarcoma, CNS neoplasms (neuroblastomas, capillary hemangioblastomas, meningiomas and cerebral metastases), melanoma, gastrointestinal and renal carcinomas, including papillary carcinoma of the kidney, and sarcomas, rhabdomyosarcoma, glioblastoma, including glioblastoma multiforme, and leiomyosarcoma.

In another aspect of the invention, the anti-RON antibodies inhibit tumor-associated angiogenesis. Stimulation of vascular endothelium by receptor tyrosine kinases is associated with vascularization of tumors. Typically, vascular endothelium is stimulated in a paracrine fashion.

Administration of the anti-RON antibody constitutes monotherapy. In other contemplated embodiments, combination therapy may be involved, wherein the anti-RON antibody is administered in combination with an anti-neoplastic agent or other agent active against the given pathological condition.

Antineoplastic agents may be administered separately or as a conjugate to the RON antibody. The anti-neoplastic agents which are presently known in the art or being evaluated can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents.

A "small organic molecule" according to the invention is defined as a conventional antineoplastic agent, e.g., one that is not comparatively large biomolecule, such as an antibody or nucleic acid. For instance, many of the known antineoplastic agents are small organic molecules, such as the topoisomerase inhibitors, among others. Thus, embodiments of the invention optionally include methods in which a topoisomerase inhibitor is administered in combination with an antibody that binds to RON. The inhibitors can be inhibitors of topoisomerase I or topoisomerase II. Topoisomerase I inhibitors include irinotecan (CPT-II), aminocamptothecin, camptothecin, DX-8951f, topotecan. Topoisomerase II inhibitors include etoposide (VP-16), and teniposide (VM-26). Other substances are currently being evaluated with respect to topoisomerase inhibitory activity and effectiveness as anti-neoplastic agents. Other small organic molecule antineoplastic agents, or chemotherapeutic agents, optionaly co-administered with the inventive antibodies, can be an alkylating agent or an anti-metabolite. Examples of alkylating agents include, but are not limited to, cisplatin, cyclophosphamide, melphalan, and dacarbazine. Additional small organic molecules include cytotoxic and/or chemotherapeutic agents such as taxol, doxorubicin, actinomycin-D, methotrexate, gemcitabine, oxyplatin, fluorouracil (5-FU), leucourin (LU), cisplatin, irinotecan (CPT-II), paclitaxel, docetaxel, vinblastine, epothilone, cisplatin/carboplatin and pegylated adriamycin. The small organic molecules may be administered in combinations such as: (CPT-II; 5-FU; LU); (Paclitaxel; 5-FU); and (CPT-II; 5-FU; LU).

The anti-neoplastic agent also includes radiation. When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of tumor being treated and the route of administration of the agent. It should be emphasized, however, that the present invention is not limited to any particular dose. Radiation may be used in conjunction with other antineoplastic agents.

In another aspect of the invention, anti-RON antibodies or antibody fragments can be chemically or biosynthetically linked to anti-tumor agents or detectable signal-producing agents, particularly when the antibody is internalized. Anti-tumor agents linked to an antibody include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods (See, e.g., Hermentin and Seiler, Behring Inst. Mitt. 82:197-215 (1988)).

The RON antibody may also be administered with radioisotopes to a cancer patient. Suitable radioisotopes for use as anti-tumor agents are also known to those skilled in the art. For example, 131I or 21 IAt may be used. These isotopes are attached to the antibody using conventional techniques (See, e.g., Pedley et al, Br. J. Cancer 68, 69-73 (1993)). Alternatively, the anti-tumor agent which is attached to the antibody is an enzyme which activates a prodrug, in this way, a prodrug is administered which remains in its inactive form until it reaches the tumor site where it is converted to its cytotoxic form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-α). The antibody targets the cytokine to the tumor so that the cytokine mediates damage to or destruction of the tumor without affecting other tissues. The cytokine is fused to the antibody at the DNA level using conventional recombinant DNA techniques. Interferons may also be used.

The present invention also provides a method of treating a non-cancer hyperproliferative disease in a mammal comprising administering to the mammal an effective amount of the antibody of the present invention. As disclosed herein, "hyperproliferative disease" is defined as a condition caused by excessive growth of non-cancer cells that express a member of the RON family of receptors. The excess cells generated by a hyperproliferative disease express RON at normal levels or they may overexpress RON.

The types of hyperproliferative diseases that can be treated in accordance with the invention are any hyperproliferative diseases that are stimulated by a ligand of RON or mutants of such ligands. Examples of hyperproliferative disease include psoriasis, actinic keratoses, and seborrheic keratoses, warts, keloid scars, and eczema. Also included are hyperproliferative diseases caused by virus infections, such as papilloma virus infection. For example, psoriasis comes in many different variations and degrees of severity. Different types of psoriasis display characteristics such as pus-like blisters (pustular psoriasis), severe sloughing of the skin (erythrodermic psoriasis), drop-like dots (guttae psoriasis) and smooth inflamed lesions (inverse psoriasis). The treatment of all types of psoriasis (e.g., psoriasis vulgaris, psoriasis pustulosa, psoriasis erythrodermica, psoriasis arthropathica, parapsoriasis, palmoplantar pustulosis) is contemplated by the invention.

For treatment of hyperproliferative disease, administration of the antibodies of the invention as described above can be combined with administration of any conventional treatment agent. For example, when the hyperproliferative disease is psoriasis, there are a variety of conventional systemic and topical agents available. Systemic agents for psoriasis include methotrexate, and oral retinoids, such as acitretin, etretinate, and isotretinoin. Other systemic treatments of psoriasis include hydroxyurea, NSAIDS, sulfasalazine, and 6-thioguanine. Antibiotics and antimicrobials can be used to treat or prevent infection that can cause psoriasis to flare and worsen. Topical agents for psoriasis include anthralin, calcipotriene, coal tar, corticosteroids, retinoids, keratolytics, and tazarotene. Topical steroids are one of the most common therapies prescribed for mild to moderate psoriasis. Topical steroids are applied to the surface of the skin, but some are injected into the psoriasis lesions.

Hyperproliferative disease treatments further include administration of anti-RON antibodies in combination with phototherapy. Phototherapy includes administration of any wavelength of light that reduces symptoms of the hyperproliferative disease, as well as photoactivation of a chemotherapeutic agent (photochemotherapy). For further discussion of treatment of hyperproliferative disorders, see WO 02/11677 (Teufel et al., describing treatment of hyperproliferative diseases with epidermal growth factor receptor antagonists).

In the present invention, any suitable method or route can be used to administer anti-RON antibodies of the invention, and optionally, to co-administer other agents, e.g., anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, injection, parenteral, infusion, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

The anti-RON antibodies, particularly for treatment of cancers, can also be administered with intracellular RTK antagonists that inhibit activity of RTKs or their associated downstream signaling elements that are involved in tumor growth or tumor-associated angiogenesis. The intracellular RTK antagonists are preferably small molecules. Some examples of small molecules include organic compounds, organometallic compounds, salts of organic compounds and organometallic compounds, and inorganic compounds. Atoms in a small molecule are linked together via covalent and ionic bonds; the former is typical for small organic compounds such as small molecule tyrosine kinase inhibitors and the latter is typical of small inorganic compounds. The arrangement of atoms in a small organic molecule may represent a chain, e.g. a carbon-carbon chain or carbon-heteroatom chain or may represent a ring containing carbon atoms, e.g. benzene or a polycyclic system, or a combination of carbon and heteroatoms, i.e., heterocycles such as a pyrimidine or quinazoline. Although small molecules can have any molecular weight they generally include molecules that would otherwise be considered biological molecules, except their molecular weight is not greater than 650 D. Small molecules include both compounds found in nature, such as hormones, neurotransmitters, nucleotides, amino acids, sugars, lipids, and their derivatives as well as compounds made synthetically, either by traditional organic synthesis, bio-mediated synthesis, or a combination thereof. See, e.g. Ganesan, Drug Discov. Today 7(1): 47-55 (January 2002); Lou, Drug Discov. Today, 6(24): 1288-1294 (December 2001).

In one embodiment, the small molecule to be used as an intracellular RTK antagonist according to the present invention is an intracellular RON antagonist that competes with ATP for binding to EGFR's intracellular binding region having a kinase domain or to proteins involved in the signal transduction pathways of EGFR activation. Examples of such signal transduction pathways include the ras-mitogen activated protein kinase (MAPK) pathway, the phosphatidylinositol-3 kinase (P13K)-Akt pathway, the stress-activated protein kinase (SAPK) pathway, and the signal transducers and activators of transcription (STAT) pathways. Non-limiting examples of proteins involved in such pathways (and to which a small molecule RON antagonist according to the present invention can bind) include GRB-2, SOS, Ras, Raf, MEK, MAPK, and matrix metalloproteinases (MMPs).

The method of treatment described herein, particularly for cancers, may also be carried out in conjunction with administration of other antibodies. For example, an antibody against EGFR, such as Erbitux® (cetuximab), may also be administered, particularly when treating colon cancer. Erbitux® MAb is a recombinant, human/mouse chimeric, monoclonal antibody that binds specifically to the extracellular domain of the human EGFR. Erbitux® is an EGFR antagonist, which blocks ligand binding to EGFR, prevents receptor activation, and inhibits growth of tumor cells that express EGFR. Erbitux® has been approved for use in combination with or without irinotecan in the treatment of patients with epidermal growth factor receptor-expressing, metastatic colorectal cancer who are refractory or can not tolerate irinotecan-based chemotherapy. Erbitux® has also been shown to be effective for treatment of psoriasis. In addition to Erbitux®, other antibodies, e.g., VEGFR antibody, IGF-IR antibody, PDGFRα antibody and PDGFRβ antibody may be used.

Other antibodies for combination use include Herceptin (trastuzumab) (against breast cancer cells that express HER2, or HER2 expression on other cancer cells) and Avastin® (bevacizumab) (antibodies that inhibit angiogenesis). Other antibodies for combination are antibodies which specifically bind human insulin-like growth (IGFR) including antibodies 2F8 and A12, as described, for example, by published international patent application, WO2005/016970, published on Feb. 24, 2005 (see, e.g., page 18, Table 1), which have the following CDR sequences:

```
Heavy Chain (2F8/A12)
CDR1    SYAIS;                      (SEQ ID NO:41)

CDR2    GIIPIFGTANYAQKFQG;          (SEQ ID NO:42)

CDR3    APLRFLEWSTQDHYYYYYMDV;      (SEQ ID NO:43)

Light Chain (2F8)
CDR1    QGDSLRSYYAS;                (SEQ ID NO:44)

CDR2    GKNNRPS;                    (SEQ ID NO:45)

CDR3    NSRDNSDNRLI;                (SEQ ID NO:46)

Light Chain (A12)
CDR1    QGDSLRSYYAT;                (SEQ ID NO:47)

CDR2    GENKRPS;                    (SEQ ID NO:48)

CDR3    KSRDGSGQHLV.                (SEQ ID NO:49)
```

The methods of treatment described herein may also be carried out with administration of other peptides. For example, variants of MSP may be administered where the variants bind to RON but do not activate RON, or at least competitively inhibit MSP. See, e.g., U.S. Publ. Appl. No. 2003/0073656.

The administration of the RON antibodies with other antibodies and/or small organic molecules may occur simultaneously, or separately, via the same or different route.

Anti-RON antibodies of the invention can be administered with RON antagonists, and/or antagonists of other RTKs, such as antibodies that block RTK ligands or otherwise inhibit the RTKS. An example of other such RTKs include EGFR, c-met and VEGFR.

In one embodiment of the present invention, an anti-RON antibody is used in combination with a VEGFR antagonist. For example, VEGFR antagonist IMC-18F1 as described in Wu, et al., Clin Cancer Res; 12(21) 6573-6584 (2006). In one embodiment of the invention, an anti-RON antibody is used in combination with a receptor antagonist that binds specifically to VEGFR-2/KDR receptor (PCT/US92/01300, filed Feb. 20, 1992; Terman et al., Oncogene 6: 1677-1683 (1991)). In another embodiment, an anti-RON antibody is used in combination with a receptor antagonist that binds specifically to VEGFR-I/Fit-I receptor (Shibuya M. et al., Oncogene 5, 519-524 (1990)). Particularly preferred are antigen-binding proteins that bind to the extracellular domain of VEGFR-1 or VEGFR-2 and block binding by ligand (VEGF or PlGF), and/or inhibit VEGF-induced or PlGF-induced activation. For example, Mab IMC-1121 binds to soluble and cell surface-expressed KDR. Mab IMC-1121 comprises the VH and VL domains obtained from a human Fab phage display library. (See, WO 03/075840). In another example, ScFv 6.12 binds to soluble and cell surface-expressed Fit-I. ScFv 6.12 comprises the VH and VL domains of mouse monoclonal antibody MAb 6.12. A hybridoma cell line producing MAb 6.12 is known and has been reported in Wang et al., Blood 104(9), 2893-2902 (2004).

Another example of such an RTK is insulin-like growth factor receptor (IGFR). In certain tumor cells, inhibition of RTK function can be compensated by upregulation of other growth factor receptor signaling pathways, and particularly by RON stimulation. Further, inhibition of IGFR signaling results in increased sensitivity of tumor cells to certain therapeutic agents. Stimulation of either RON or IGFR results in phosphorylation of common downstream signal transduction molecules, including Akt and p44/42, although to different extents. Accordingly, in an embodiment of the invention, an IGFR antagonist (e.g., an antibody that binds to IGF or IGFR and inhibits the receptor) is coadministered with an antibody of the invention, thereby blocking a second input into the common downstream signaling pathway (e.g., inhibiting activation of Akt and/or p44/42). An example of a human antibody specific for IGFR is IMC-A12 (See, WO 2005/016970).

Another receptor that may be targeted in combination with RON is EGFR. EGFR may be targeted with an antibody such as Erbitux® as described above, or with a small organic molecule. One example of a small molecule RTK antagonist is IRESSA™ (ZD 1939), which is a quinozaline derivative that functions as an ATP-mimetic to inhibit EGFR. See, U.S. Pat. No. 5,616,582 (Zeneca Limited); WO 96/33980 (Zeneca Limited) at p. 4; see also, Rowinsky et al., Abstract 5 presented at the 37th Annual Meeting of ASCO, San Francisco, Calif., 12-15 May 2001; Anido et al, Abstract 1712 presented at the 37th Annual Meeting of ASCO, San Francisco, Calif., 12-15 May 2001. Another examples of a small molecule EGFR antagonist is TARCEVA™ (OSI-774), which is a 4-(substituted phenylamino)quinozaline derivative [6,7-Bis (2~methoxy-ethoxy)-quinazolin-4-yl]-(3-ethynyl-phenyl) amine hydrochloride] EGFR inhibitor. See, WO 96/30347 (Pfizer Inc.) at, for example, page 2, line 12 through page 4, line 34 and page 19, lines 14-17. See also, Moyer et al, Cancer Res., 57: 4838-48 (1997); Pollack et al, J. Pharmacol, 291: 739-48 (1999). TARCEVA™ may function by inhibiting phosphorylation of EGFR and its downstream PI3/Akt and MAP (mitogen activated protein) kinase signal transduction pathways resulting in p27-mediated cell-cycle arrest. See Hidalgo et al., Abstract 281 presented at the 37th Annual Meeting of ASCO, San Francisco, Calif., 12-15 May 2001. The above small organic molecules may also inhibit RON.

Other examples of growth factor receptors involved in tumorigenesis are the receptors for platelet-derived growth factor (PDGF), nerve growth factor (NGF), and fibroblast growth factor (FGF). These receptors may be targeted in combination with RON.

In another embodiment, the anti-RON antibody can be administered in combination with one or more suitable adjuvants, such as, for example, cytokines (IL-10 and IL-13, for example) or other immune stimulators, such as, but not limited to, chemokine, tumor-associated antigens, and peptides.

In a combination therapy, the anti-RON antibody is administered before, during, substantially simultaneously with, or after commencing therapy with another agent, as well as any combination thereof, i.e., before and during, before and after, during and after, or before, during and after commencing the anti-neoplastic agent therapy. For example, the anti-RON antibody can be administered between 1 and 30 days, or between 3 and 20 days, or between 5 and 12 days before commencing radiation therapy. In one embodiment of the invention, chemotherapy is administered concurrently with or subsequent to antibody therapy.

The invention further contemplates RON antibodies or antibody fragments of the invention to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is avidin and biotin. In a preferred embodiment, biotin is conjugated to an antigen-binding protein of the invention, and thereby provides a target for an anti-tumor agent or other moiety which is conjugated to avidin or streptavidin. Alternatively, biotin or another such moiety is linked to an antigen-binding protein of the invention and used as a reporter, for example in a diagnostic system where a detectable signal-producing agent is conjugated to avidin or streptavidin.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

Moreover, included within the scope of the present invention is use of the present antibodies in vivo and in vitro for investigative or diagnostic methods, which are well known in the art. The diagnostic methods include kits, which contain antibodies of the present invention. Such kits might be useful for identification of individuals at risk for certain type of cancers by detecting over-expression of RON on cells of such individuals. Additionally, the antibodies of the present invention may be used in the laboratory for research due to their ability to identify RON.

The present invention also includes kits, e.g., kits for inhibiting tumor growth and/or tumor-associated angiogenesis comprising a therapeutically effective amount of a human anti-EGFR antibody. The kits can further contain any suitable antagonist of, for example, another growth factor receptor involved in tumorigenesis or angiogenesis (e.g., VEGFR-1/ Flt-1, VEGFR-2, PDGFR, IGFR, NGFR, EGFR, FGFR, etc, as described above). Alternatively, or in addition, the kits of the present invention can further comprise an anti-neoplastic agent. Examples of suitable anti-neoplastic agents in the context of the present invention have been described herein. The kits of the present invention can further comprise an adjuvant; examples have also been described above.

The present invention further provides the method of identifying and isolating antibodies having the same functionality of RON6 or RON8, or fragments thereof, wherein the screening of a library includes providing an affinity matrix having RON containing ligand binding function bound to a solid support, contacting the affinity matrix with the library of antibody fragments, and separating the antibody fragments that bind to the affinity matrix from the antibody fragments that do not bind the affinity matrix.

Solid support means a non-aqueous matrix to which the RON can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

The present invention also provides for methods of treatment where a RON antibody other than that provided in the present invention is used.

Reference is made herein in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the instant description, numerous specific details are set forth in order to provide a thorough understanding of the present invention. The present invention may be practiced without some or all of these specific details. In other instances, well known process operations have not been described in detail, in order not to unnecessarily obscure the present invention.

All of the above U.S. patents, U.S. patent application publications, U.S. patent applications, and foreign patents, foreign patent applications referred to in this specification, are incorporated herein by reference in their entirety.

All publications cited in the specification are indicative of the level of skill of those skilled in the art to which this invention pertains. All these publications are herein incorporated by reference in their entirety to the same extent as if each individual publication were specifically and individually indicated to be incorporated by reference.

EXAMPLES

The following examples are offered for illustrative purposes only, and are not intended to limit the scope of the present invention in any way. The examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989) *Molecular Cloning: A laboratory Manual*, 2$^{nd}$ Edition, Cold Spring Harbor Laboratory Press.

Materials and Methods
Development and Characteristics of Two Anti-RON Antibodies RON6 AND RON8.

Example 1

Generation of Anti-RON Antibodies

Human anti-RON monoclonal antibodies (referred to herein as RON6 and RON8) were generated by standard hybridoma technology (Harlow & Lane, ed., *Antibodies: A Laboratory Manual*, Cold Spring Harbor, 211-213 (1998), which is incorporated by reference herein) using HuMAb mice (Medarex, San Jose, Calif.), which produce human immunoglobulin gamma heavy and kappa light chains. HuMAb mice were immunized subcutaneously (s.c.) with RON extracellular domain fragment, RE7 cells and MDCK cells overexpressing the human RON receptor in complete Freund's adjuvant. Animals were intraperitoneally (i.p.) boosted three times with the same RON protein in incomplete Freund's adjuvant before fusion. The animals were rested for a month before they received the final i.p. boost of 25 micrograms of RON protein in phosphate buffer solution (PBS). Four days later, splenocytes were harvested from the immunized mouse and fused with P3-X63-Ag8.653 Bcl-2 transfectant plasmacytoma cells using polyethylene glycol (PEG, MW: 1450 KD). After fusion, the cells were resuspended in HAT (hypoxanthine, aminopterin, thymidine) medium supplemented with 10% fetal bovine serum (FBS) and distributed to 96 well plates at a density of 200 microliters per well for establishment of hybridoma cells. At day 6 postfusion, 100 microliters of medium was aspirated and replaced with 100 microliters of fresh medium.

It should be noted that 180 hybridoma clones were identified from one fusion to be positive clones that produced antibodies reactive with rhu-RON protein. Of the 180 binding positives, only five clones were identified having blocking activity. Of these five, only two, RON6 and RON8, were selected for further development based on their superior binding specificity.

Subcloning of those hybridoma clones demonstrating blocking activity was performed three times to establish the monoclonal hybridoma cell lines producing mAbs directed against RON.

The clones with blocking activity were further validated for the selection of stronger blocking activity. The clones designated as RON6 and RON8, had stronger blocking activity with $IC_{50}$ of 2-3 nM as measured in ELISA and high affinity (KD value=45 and 23 pM, respectively). These two clones were selected for further development.

The RON6 and RON8 antibodies are IgG antibodies and the respective heavy and light chains have been sequenced. The structure of each antibody is readily appreciated from the provided figures and corresponding sequences, as follows.

Structure of RON6

The RON6 antibody includes two heavy chains, each as illustrated by FIGS. 2A, 2B and 2C, taken together as SEQ ID NO:10, which is encoded by the DNA sequence of SEQ ID NO:9. It should be noted that the first 19 residues/codon triplets of FIG. 2A represent the secretory signal sequence, not present in the mature antibody chain.

The RON6 antibody also includes two light chains, which are illustrated by FIGS. 2D-2E, taken together as SEQ ID NO:12, which is encoded by the DNA sequence of SEQ ID NO:11. It should be noted that the first 19 residues/codon triplets of FIG. 2D represent the secretory signal sequence, not present in the mature antibody chain.

Structure of RON8

The RON8 antibody includes includes two heavy chains, each as illustrated by FIGS. 3A, 3B and 3C, taken together as SEQ ID NO:14, which is encoded by the DNA sequence of SEQ ID NO:13. It should be noted that the first 19 residues/codon triplets of FIG. 3A represent the secretory signal sequence, not present in the mature antibody chain.

The RON8 antibody also includes two light chains, which are illustrated by FIGS. 3D-3E, taken together as SEQ ID NO:16, which is encoded by the DNA sequence of SEQ ID NO:15. It should be noted that the first 19 residues/codon triplets of FIG. 3D represent the secretory signal sequence, not present in the mature antibody chain.

Example 2

Anti-RON Antibodies from Example 1 Bind to RON and Inhibit RON Binding to its Ligand (MSP)

Binding ELISA: At day 10-12 post-fusion, the hybridomas were screened for antibody production and specific binding activity of culture supernatant with rh-RON protein in ELISA-based binding and blocking assays. Maxi-sorp 96-well microtiter plates (Nunc) were coated with (1 µg/ml× 10041) rh-RON protein (R&D Systems) at RT for 1.5 hours. After washing the wells, they were blocked with 3% PBS/milk. Anti-RON antibodies derived from the hybridoma supernatants were then added to the coated wells and allowed to incubate for 1.5 h at RT. After several washes, a 1:1000 dilution of the anti-human IgG-HRP conjugated antibody was added to the plates for 1.5 h at RT in order to detect the positive binding. The positive hybridomas were subcloned three times by a limiting dilution culture for establishment of monoclonal hybridomas.

ELISA to Detect Antibodies That Block the MSP/RON Interaction: Maxi-sorp 96-well microtiter plates (Nunc) were coated with (1 µg/ml×100 µl) MSP (R&D Systems) at RT for 1.5 hours. After washing the wells, they were blocked with 3% PBS/milk. Anti-RON antibodies derived from the hybridoma supernatants were first incubated for 1 h at RT with rh-RON and then added to the MSP-coated wells. After 1.5 h of incubation RT followed by several washes, a 1:1000 dilution of the anti-human IgG-HRP conjugated antibody was added to the plates for 1.5 h at RT in order to detect which anti-RON could block the MSP/RON interaction.

ELISA to Detect RON8 Blocking of MSP Binding to RON: ELISA plates were coated with 100 ng/well carrier-free MSP (R&D Systems) overnight at 4° C. on a rocker. The plate was washed once with 0.2% PBS/T and blocked for 2 hours at 37° C. with 150 µL/well 3% milk. A 15 µg/mL dilution of RON8 was prepared and serially diluted across another ELISA plate. To the RON8, was added 100 ng/well recombinant human MSPR (R&D Systems). The RON8/rh-MSPR complex was allowed to form for 2 hours at room temperature on a rocker. Next, the MSP-coated ELISA plate was washed once with 0.2% PBS/T and 100 µL of the RON8/rh-MSPR complex were added per well. After a 1.5-hour incubation at room temperature, the plate was washed five times with 0.2% PBS/T and incubated for 1 hour at room temperature with a 1:2,000 dilution of anti-His-tag HRP antibody (Sigma), which recognizes a His tag on the recombinant human MSPR protein. The plate was washed five times with 0.2% PBS/T and 100-AL substrate was added per well until a yellow color developed. The reaction was stopped with 50 µL of 1N $H_2SO4$ and the absorbance at 450 nm determined with a standard plate reader. The results of which are illustrated by FIG. 6A depict the solid-phase blocking characteristic of RON8. The ELISA data determined the IC50 value of RON8 needed to block the interaction of recombinant human RON protein to immobilized recombinant human MSP.

Cell Migration. To determine whether RON8 could block the migration of H596 lung cancer cells (ATCC, Manassas, Va.) induced by MSP, we used 24-well cell culture inserts, containing porous translucent polyethylene terephthalate track-etched membranes (8.0 Am pore size; Becton Dickinson Falcon). Before the assay was performed, the undersides of the porous membranes were coated with collagen by placing them into a 24-well Falcon plate filled with 70041 of Vitrogen-100 purified collagen solution (25 µg/mL; Cohesion, Palo Alto, Calif.). The inserts were left for 1 hour at 4° C. and then placed in a new 24-well plate. Next, $6\times10^5$ viable cells that had been serum starved for 24 hours, were rinsed once with PBS and then seeded into the upper chamber of the cell culture insert in 300 µL of serum-free medium. MSP was added to the lower chamber in 700 µl of serum-free medium for 24 hours at 37° C. to induce cell migration through the collagen-coated porous membrane. 0% serum was used as a negative control and 10% serum was used as a positive control for cell migration. Before the addition of MSP, RON8 was added to some of the upper chambers for 1 hour, to determine if it could inhibit the MSP-induced migration of H596 cells. At the conclusion of the assay, migrated cells adhering to the underside of the collagen-coated membrane were stained with Hoechst dye (2 µg/ml; Invitrogen-Molecular Probes, Carlsbad, Calif.), imaged by fluorescence microscopy at 100× magnification and counted using Image-Pro Plus software. FIG. 6B illustrates the ability of RON8 to inhibit cell migration of H596 lung cancer cells.

Ability of RON8 to Inhibit Migration in an In Vitro Wound Healing Assay. A scratch was made in the monolayer of H292 lung cancer cells. RON8 was added to determine whether it could inhibit the ability of MSP to induce the migration of cells to fill the wound. H292 lung cancer cells were seeded at $2.5\times10^5$ cells/well in a Becton Dickinson Falcon 6-well cell culture plate and allowed to grow overnight to confluence. Cells were serum starved for 48 hours. Before the addition of MSP, some wells were pre-incubated with the RON8 antibody for 1 hour before wound inflication. At the start of the assay, a small wound was inflicted with a 200 µl plastic pipette tip. Next, cells were incubated for 24 hours with and without the presence of MSP in serum-free medium plus RON8 antibody. 0% serum was used as a negative control and 10% serum was used as a positive control for cell migration into the wound. After the 24 hour incubation, the cells were imaged by bright field microscopy at 40× magnification. It was observed that 100 nM of RON8 inhibited the migration of cells to fill in the wound, thereby illustrating the ability of RON8 to inhibit cell migration in an in vitro model.

Ability of RON8 to Inhibit Proliferation. FIG. 6C illustrates RON8 inhibition of MSP-induced DNA synthesis in BXPC3 pancreatic cancer cells. FIG. 6C(1) illustrates MSP stimulation of [3H]-Thymidine incorporation, a measure of DNA synthesis. Tumor cells (10,000 per well) were plated into 96-well tissue culture plates and rendered quiescent. The cells were stimulated with MSP for 20 hours. [3H]-Thymidine (0.25 mCi) was added to each well and incubated for an additional 4 h. DNA incorporated radioactivity was determined with a scintillation counter. Points, mean of duplicate samples; bars, SD. FIG. 6C(2) illustrates the system wherein; cells were pretreated with RON8 for 1 hour prior to the addition of MSP.

BIAcore Analysis. The binding kinetics of the antibodies to the RON proteins was determined by using a BIACORE 3000 (BIAcore, Piscataway, N.J.). Recombinant RON-Fc was immobilized onto a sensor chip, and antibody was injected at various concentrations. Sensorgrams were obtained and evaluated using BIA Evaluation 2.0 software to determine rate constants. The affinity constant, $K_D$, was calculated from the ratio of the rate constants $K_{off}/K_{on}$. The "$K_{on}$, $M^{-1}.S^{-1}$" and "$K_{off}$, $S^{-1}$" rates of the interaction were used to determine the affinity (Kd, M) of the antibody/receptor interaction. The $K_d$, $K_{on}$, and $K_{off}$ rates for RON6 were 4.1e-11, 2.2e6 and 8.6e-5. For RON8 they were: 3.2e-11, 6.1e6 and 2.0e-4

Flow Cytometry of RON Cell Surface Expression. One million cells from adherent cancer cell lines were incubated in PBS+5% FCS for 30 minutes with 5 micrograms RON8 at 4° C. After a wash in PBS+5% FCS, cells were incubated with anti-human IgG phycoerythrin-conjugated secondary antibody (Jackson Immuno Research) for 30 minutes at 4° C. After a PBS+5% FCS wash, cells were analyzed by flow cytometry using a FACSvantage SE flow cytometer (Becton Dickinson).

Western Blotting and Immunoprecipitation. Cells were plated into 10-cm or 6-well culture dishes and grown to 70-80% confluence. Monolayers were washed twice in PBS and cultured overnight in serum-free medium. Antibody was then added and incubated at 37° C. for 60-120 min. Cells were stimulated with MSP ligand for 10 min and then placed on ice and washed with ice-cold PBS. The cells were lysed in 50 mM Tris-HCl (pH 7.4), 150 mM NaCl, 1% Triton X-100, 1 mM EDTA, 1 mM phenylmethylsulfonyl fluoride, 0.5 mM $Na_3VO_4$, 1 µg/ml leupeptin, 1 µg/ml pepstatin, and 1 µg/ml aprotinin on ice for 10 min. The lysate was clarified by centrifugation at 4° C. Solubilized RON was then immunoprecipitated from the lysate. Antibody RON, clone C-20 (Santa Cruz Biotechnology, Santa Cruz, Calif.) or RON6 and RON8 were incubated with 400 µl of lysate at 4 µg/ml overnight at 4° C. Immune complexes were precipitated by the addition of protein A-agarose beads for 2 h at 4° C., pelleted, and washed three times with lysis buffer. Immunoprecipitates bound to the protein A-agarose beads were stripped into denaturing gel sample buffer. Lysates or immunoprecipitates were processed for denaturing gel electrophoresis and run on a 4-12% acrylamide gel and blotted to nitrocellulose membrane by Western blot. Tyrosine-phosphorylated protein was detected on the blot using an anti-phosphoRON antibody (Biosource) and an anti-mouse-horseradish peroxidase secondary antibody. RON was detected with monoclonal antibody RON C-20 (Santa Cruz Biotechnology. Phospho-Akt and total Akt antibodies were obtained from PharMingen (BD Biosciences, San Diego, Calif.) For MAPK phosphorylation, phospho-p44/42 and total p44/42 antibodies were purchased from Cell Signaling Technology. Bands were visualized with the enhanced chemiluminescence reagent (Amersham Pharmacia Biotech) on X-ray film (Eastman Kodak, Rochester, N.Y.).

ELISA for Determination of IC50 and ED50 Values

The ability of the anti-RON antibodies, RON6 and RON8, to bind to recombinant human RON receptor and to block the MSP/RON interaction were measured using ELISA. With the receptor immobilized to an ELISA plate, the ED50 values for binding of RON6 and RON8 to RON were 4.2 pM and 2.1 pM respectively. Using the same ELISA format, the two antibodies were tested for their ability to block MSP/RON interactions. The measured $IC_{50}$ values were 46 pM for RON6 and 62 pM for RON8.

Human Tumor Xenograft Model. Tumor xenografts were established by s.c. injection of $5 \times 10^6$ cells mixed in Matrigel (Collaborative Research Biochemicals, Bedford, Mass.) into the left flank of 5-6-week-old female athymic (nu/nu) mice (Charles River Laboratories, Wilmington, Mass.). Tumors were allowed to reach 150-300 $mm^3$ in size, and then mice were randomized into groups of 12 animals each. Mice were treated by i.p. injection every 3 days with control antibody (human IgG) or RON6 and RON8 antibodies. Treatment of animals was continued for the duration of the study. Tumors were measured twice each week with calipers, and tumor volumes were calculated by the following formula: ($\pi/6$ (w1× w2×w2)), where w1 represents the largest tumor diameter, and w2 represents the smallest tumor diameter. Tumor volumes were analyzed using the Mann-Whitney U test and computed using the statistical package in SigmaStat (version 2.03; Jandel Scientific, San Rafeal, Calif.).

Example 3

Confirmation of Tumor Inhibition in Human Tumor Xenograft Model

The effectiveness of the RON6 AND RON8 antibodies in suppressing tumor growth, in vivo, was confirmed in four different tumor cells by employing the mouse xenograft methods described by Example 2, above. The tumor cells were as follows. H-292 cells, derived from a lung tumor and obtained from the American Type Culture Collection (Manassas, Va.). HT-29 cells, derived from a colon tumor and obtained from the American Type Culture Collection (Manassas, Va.). BxPC3 cells, derived from a pancreatic tumor and obtained from the American Type Culture Collection (Manassas, Va.). JIMT cells, derived from a breast tumor and obtained from the American Type Culture Collection (Manassas, Va.).

Using the above described xenograft methods, H-292 cells were injected into a total of 24 mice. Twelve mice were treated with the RON6 antibody at 60 mg/kg and 12 were treated with saline, as a control. A significant inhibition of tumor volume was observed, relative to control, as illustrated by FIG. 4A. The experiment was also conducted with 40 mice, divided into four groups that were treated with saline and RON8 antibody at 60 mg/kg, 20 mg/kg and 2 mg/kg, respectively. A significant inhibition of tumor volume, relative to control, was observed, as illustrated by FIG. 4B. As can be seen in FIG. 4B, this experiment also confirmed that the response increased with the dose of antibody.

Using the above described xenograft methods, HT-29 cells were injected into a total of 24 mice. Twelve mice were treated with the RON6 antibody at 60 mg/kg and 12 were treated with saline. A significant inhibition of tumor volume was observed, relative to control, as illustrated by FIG. 4C. The same experiment was also conducted with another group of 40 mice, that was divided into four groups that were treated with saline or RON8 antibody at 60 mg/kg, 20 mg/kg and 2 mg/kg, respectively. A significant inhibition of tumor volume was observed, relative to control, as illustrated by FIG. 4D. As can be seen in FIG. 4D, this experiment also confirmed that the response increased with the dose of antibody.

Figure 4E:
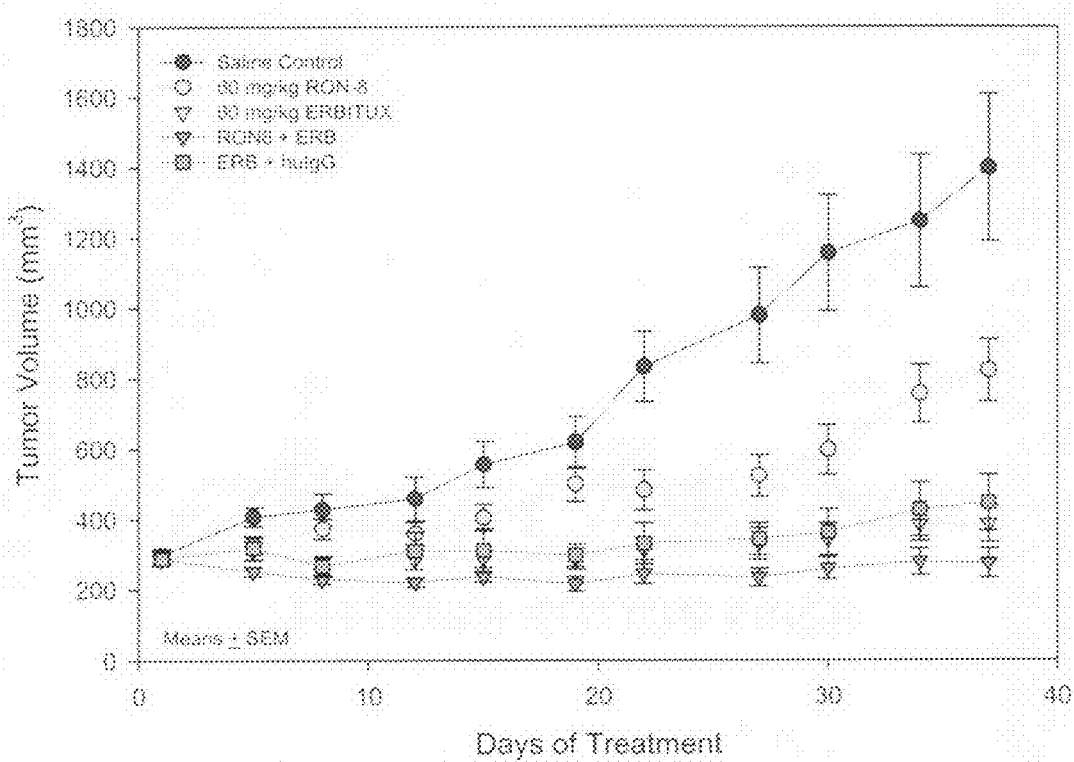

Using the above described xenograft methods, BxPC3 cells were injected into a total of 60 mice. The mice were divided into five groups (12/group) and treatment was as follows: saline, 60 mg/kg of RON8, 60 mg/kg of Erbitux® (obtained from ImClone Systems, Inc.), 60 mg/kg of RON8 and 60 mg/kg of Erbitux® and 60 mg/kg of Erbitux® and 60 mg/kg of huIgG (control IgG, obtained from Meridian Life Sciences). The results, illustrated by FIG. 4E, confirm that RON-8 increases the antitumor effects of cetuximab in the pancreatic BxPC-3 model (p value of 0.06 using one sided repeated measures ANOVA).

Figure 4F:
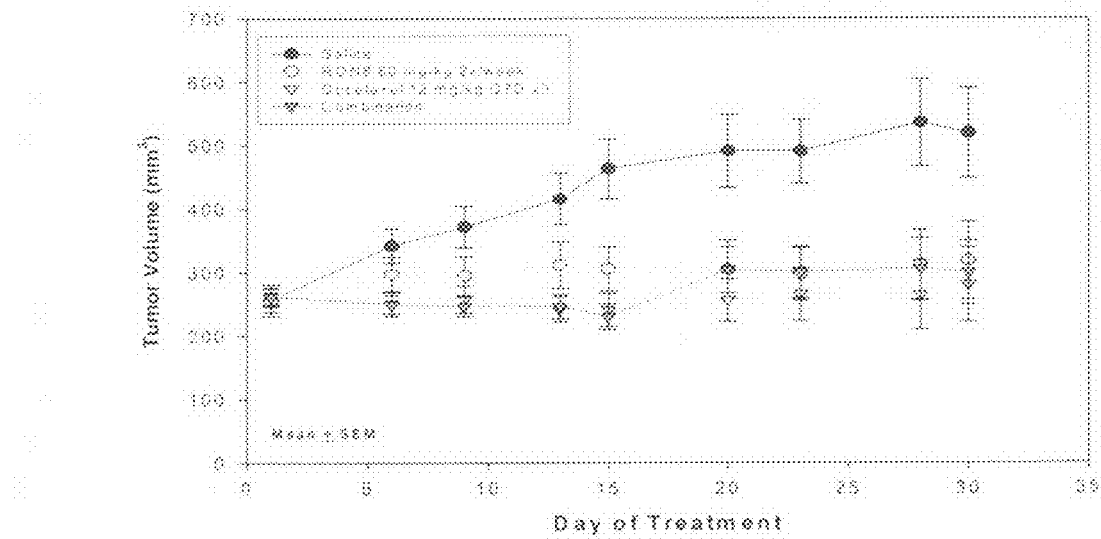

Using the above described xenograft methods, JIMT-1 breast cancer cells were injected subcutaneously into nude mice and allowed to grow to approximately 250 $mm^3$. Tumor volume was plotted during the course of treatment with Control (Saline), RON8 (60 mg/kg, 2×/week), docetaxel, or the combination of docetaxel+RON8. Mean+/−SEM is plotted. The results, illustrated by FIG. 4F, confirm that RON-8 inhibits the growth of breast tumor xenografts in nude mice in the breast JIMT-1 model.

CITED PUBLICATIONS

1) Wang, M. H., Kurtz, A. L., Chen, Y. (2000b). Identification of a novel splicing product of the RON receptor tyrosine kinase in human colorectal carcinoma cells. *Carcinogenesis* 21, 1507-1512.
2) Leonard, E. J., Danilkovitch, A. (2000). Macrophage stimulating protein. *Adv. Cancer Res.* 77, 139-167.
3) Skeel, A., Leonard, E. J. (1994). Action and target cell specificity of human macrophage-stimulating protein (MSP). *J. Immunol.* 152, 4618-4623.
4) Leonard, E. J., Skeel, A. (1976). A serum protein that stimulates macrophage movement, chemotaxis and spreading. *Exp. Cell Res.* 102, 434-438.
5) Iwama, A., Wang, M. H., Yamaguchi, N., Ohno, N., Okano, K., Sudo, T., Takeya, M., Gervais, F., Morissette, C., Leonard, E. J. (1995). Terminal differentiation of murine resident peritoneal macrophages is characterized by expression of the STK protein tyrosine kinase, a receptor for macrophage-stimulating protein. *Blood* 86, 3394-3403.
6) Wang, M. H., Cox, G. W., Yoshimura, T., Sheffler, L. A., Skeel, A., Leonard, E. J. (1994a). Macrophage-stimulating protein inhibits induction of nitric oxide production by endotoxin- or cytokine-stimulated mouse macrophages. *J. Biol. Chem.* 269, 14027-14031.
7) Wang, M. H., Dlugosz, A. A., Sun, Y., Suda, T., Skeel, A., Leonard, E. J. (1996a). Macrophage-stimulating protein induces proliferation and migration of murine keratinocytes. *Exp. Cell Res.* 226, 39-46.
8) Wang, M. H., Montero-Julian, F. A., Dauny, I., Leonard, E. J. (1996b). Requirement of phosphatidylinositol-3 kinase for epithelial cell migration activated by human macrophage stimulating protein. *Oncogene* 13, 2167-2175.
9) Okino, T., Egami, H., Ohmachi, H., Takai, E., Tamori, Y., Nakagawa, K., Nakano, S., Akagi, J., Sakamoto, O., Suda, T., Ogawa, M. (1999). Presence of RON receptor tyrosine kinase and its splicing variant in malignant and non-malignant human colonic mucosa. *Int. J. Oncol.* 15, 709-714.
10) Chen, Y. Q., Zhou, Y. Q., Angeloni, D., Kurtz, A. L., Qiang, X. Z., Wang, M. H. (2000). Overexpression and activation of the RON receptor tyrosine kinase in a panel of human colorectal carcinoma cell lines. *Exp. Cell Res.* 261, 229-238.
11) Wang, M. H., Kurtz, A. L., Chen, Y. (2000b). Identification of a novel splicing product of the RON receptor tyrosine kinase in human colorectal carcinoma cells. *Carcinogenesis* 21, 1507-1512.
12) Willett, C. G., Wang, M. H., Emanuel, R. L., Graham, S. A., Smith, D. I., Shridhar, V., Sugarbaker, D. J., Sunday, M. E. (1998). Macrophage-stimulating protein and its receptor in non-small-cell lung tumors: induction of receptor tyrosine phosphorylation and cell migration. *Am. J. Respir. Cell Mol. Biol.* 18, 489-496.
13) Maggiora, P., Marchio, S., Stella, M. C., Giai, M., Belfiore, A., De Bortoli, M., Di Renzo, M. F., Costantino, A., Sismondi, P., Comoglio, P. M. (1998). Overexpression of the RON gene in human breast carcinoma. *Oncogene* 16, 2927-2933.
14) Chen, Y Q, Zhou, Y Q, Fisher, J H, Wang M-H. (2002). Targeted expression of the receptor tyrosine kinase RON in distal lung epithelial cells results in multiple tumor formation: oncogenic potential of RON in vivo. *Oncogene* 21, 6382-6386.
15) Chen Y Q, Zhou Y Q, Fu L H, Wang D, Wang M H. (2002). Multiple pulmonary adenomas in the lung of transgenic mice overexpressing the RON receptor tyrosine kinase. *Carcinogenesis* 23, 1811-1819.
16) Santoro M M, Collesi C, Grisendi S, Gaudino G, Comoglio P (1996). Constitutive Activation of the RON Gene Promotes Invasive Growth but Not Transformation. *Molecular and Cellular Biology*, December, p. 7072-7083.
17) O'Toole J. M., Rabenau K. E., Burns K., Lu D., Mangalampalli V., Balderes P., Covino N., Bassi R., Prewett M., Gottfredsen K. J., Thobe M.n., Cheng Y., Li Y., Hicklin D. J., Zhu Z., Waltz S. E., Hayman M. J., Ludwig D. L. and Pereira, D. S. (2006) Therapeutic Implications of a Human Neutralizing Antibody to the Macrophage-Stimulating Protein Receptor Tyrosine Kinase (RON), a c-MET Family Member. *Cancer Research* 66: (18), 9162-9170.
18) Patton K T, Tretiakova M S, Yao J L, Papavero V, Huo L, Adley B P, Wu G, Huang J, Pins M R, Teh B T, Yang X J. (2004) Expression of RON Proto-oncogene in Renal Oncocytoma and Chromophobe Renal Cell Carcinoma. *Am J Surg Pathol.*, August 28 (8): 1045-50.
19) Suzuki Y, Funakoshi H, Machide M, Matsumoto K, Nakamura T. (2008) Regulation of cell migration and cytokine production by HGF-like protein (HLP)/macrophage stimulating protein (MSP) in primary microglia. *Biomed Res.* April; 29 (2):77-84.
20) Gaudino G, Avantaggiato V, Follenzi A, Acampora D, Simeone A, Comoglio P M (1995) The proto-oncogene RON is involved in development of epithelial, bone and neuro-endocrine tissues. *Oncogene.* December 21; 11(12): 2627-37.

---

The invention claimed is:

1. An antibody or fragment thereof that specifically binds to a human RON protein, wherein said antibody or fragment thereof comprises a CDRH1 having the sequence GFTFSSYLMT (SEQ ID NO: 29), a CDRH2 having the sequence NIKQDGSEKYYVDSVKG (SEQ ID NO: 31), a CDRH3 having the sequence DGYSSGRHYGMDV (SEQ ID NO: 33), a CDRL1 having the sequence RASQSVSRYLA (SEQ ID NO: 35), a CDRL2 having the sequence DASNRAT (SEQ ID NO: 37) and a CDRL3 having the sequence QQRSNWPRT (SEQ ID NO: 39).

2. The antibody or fragment thereof of claim 1 wherein said antibody or fragment thereof comprises a heavy chain variable region having the sequence EVQLVESGGGLVQPGGSLRLSCAASG-FTFSSYLMTWVRQAPGKGLEWVANIKQDGSEK YYVDSVKGRFTISRDNAKNSLNLQMNSL-RAEDTAVYYCTRDGYSSGRHYGMDVWGQG TTVIVSS (SEQ ID NO: 6) and a light chain variable region having the sequence EIVLTQSPATLSLSPGERATLSCRASQS-VSRYLAWYQQKPGQAPRLLIYDASNRATGIPAR FSGSGSGTDFTLTISSLEPEDFAVYYC-QQRSNWPRTFGQGTKVEIK (SEQ ID NO: 8).

3. The antibody or fragment thereof of claim 1 wherein said antibody or fragment thereof comprises a heavy chain variable region having the sequence EVQLVESGGGLVQPGGSLRLSCAASG-FTFSSYLMTWVRQAPGKGLEWVANIKQDGSEK YYVDSVKGRFTISRDNAKNSLNLQMNSL-RAEDTAVYYCTRDGYSSGRHYGMDVWGQG TTVIVSS (SEQ ID NO: 6) or a light chain variable region having the sequence EIVLTQSPATLSLSPGERATLSCRASQS-VSRYLAWYQQKPGQAPRLLIYDASNRATGIPAR FSGSGSGTDFTLTISSLEPEDFAVYYC-QQRSNWPRTFGQGTKVEIK (SEQ ID NO: 8).

4. The antibody or fragment thereof of claim 1 wherein said antibody or fragment thereof comprises a heavy chain having the sequence EVQLVESGGGLVQPGGSLRLSCAASG-FTFSSYLMTWVRQAPGKGLEWVANIKQDGSEK YYVDSVKGRFTISRDNAKNSLNLQMNSL-RAEDTAVYYCTRDGYSSGRHYGMDVWGQG TTVIVSSASTKGPSVFPLAPSSKSTSGG-
TAALGCLVKDYFPEPVTVSWNSGALTSGVHTFP
AVLQSSGLYSLSSVVTVPSSSLGTQTY-
ICNVNHKPSNTKVDKRVEPKSCDKTHTCPPCPAP
ELLGGPSVFLFPPKPKDTLMISRTPE-
VTCVVVDVSHEDPEVKFNWYVDGVEVHNAKTKP
REEQYNSTYRVVSVLTVLHQDWL-
NGKEYKCKVSNKALPAPIEKTISKAKGQPREPQVYT
LPPSREEMTKNQVSLTCLVKGFYPSDIA-
VEWESNGQPENNYKTTPPVLDSDGSFFLYSKL
TVDKSRWQQGNVFSCSVMHEALH-
NHYTQKSLSLSPGK (SEQ ID NO: 50)
and a light chain having the sequence
EIVLTQSPATLSLSPGERATLSCRASQS-
VSRYLAWYQQKPGQAPRLLIYDASNRATGIPAR
FSGSGSGTDFTLTISSLEPEDFAVYYC-
QQRSNWPRTFGQGTKVEIKRTVAAPSVFIFPPSDE
QLKSGTASVVCLLNNFYPREAKVQWKVD-
NALQSGNSQESVTEQDSKDSTYSLSSTLTLS
KADYEKHKVYACEVTHQGLSSPVTKSFNRGEC (SEQ
ID NO: 51).

5. The antibody or fragment thereof of claim 1 comprising two heavy chains having the sequence
EVQLVESGGGLVQPGGSLRLSCAASG-
FTFSSYLMTWVRQAPGKGLEWVANIKQDGSEK
YYVDSVKGRFTISRDNAKNSLNLQMNSL-
RAEDTAVYYCTRDGYSSGRHYGMDVWGQG
TTVIVSSASTKGPSVFPLAPSSKSTSGG-
TAALGCLVKDYFPEPVTVSWNSGALTSGVHTFP
AVLQSSGLYSLSSVVTVPSSSLGTQTY-
ICNVNHKPSNTKVDKRVEPKSCDKTHTCPPCPAP
ELLGGPSVFLFPPKPKDTLMISRTPE-
VTCVVVDVSHEDPEVKFNWYVDGVEVHNAKTKP
REEQYNSTYRVVSVLTVLHQDWL-
NGKEYKCKVSNKALPAPIEKTISKAKGQPREPQVYT
LPPSREEMTKNQVSLTCLVKGFYPSDIA-
VEWESNGQPENNYKTTPPVLDSDGSFFLYSKL
TVDKSRWQQGNVFSCSVMHEALH-
NHYTQKSLSLSPGK (SEQ ID NO: 50)
and two light chains having the sequence
EIVLTQSPATLSLSPGERATLSCRASQS-
VSRYLAWYQQKPGQAPRLLIYDASNRATGIPAR
FSGSGSGTDFTLTISSLEPEDFAVYYC-
QQRSNWPRTFGQGTKVEIKRTVAAPSVFIFPPSDE
QLKSGTASVVCLLNNFYPREAKVQWKVD-
NALQSGNSQESVTEQDSKDSTYSLSSTLTLS
KADYEKHKVYACEVTHQGLSSPVTKSFNRGEC (SEQ
ID NO: 51).

6. A pharmaceutical composition comprising the antibody or fragment thereof of claim 1 together with a pharmaceutically acceptable carrier, excipient or stabilizer.

7. A pharmaceutical composition comprising the antibody or fragment thereof of claim 5 together with a pharmaceutically acceptable carrier, excipient or stabilizer.

\* \* \* \* \*